(12) United States Patent
Kashima

(10) Patent No.: US 9,311,701 B2
(45) Date of Patent: Apr. 12, 2016

(54) IMAGE PROCESSING APPARATUS AND IMAGE PROCESSING METHOD

(71) Applicant: Sony Corporation, Tokyo (JP)

(72) Inventor: Koji Kashima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 244 days.

(21) Appl. No.: 13/891,327

(22) Filed: May 10, 2013

(65) Prior Publication Data
US 2013/0307845 A1 Nov. 21, 2013

(30) Foreign Application Priority Data

May 18, 2012 (JP) .................................. 2012-114010

(51) Int. Cl.
G06T 7/00 (2006.01)
G06T 15/00 (2011.01)
G06T 11/20 (2006.01)
G06T 19/00 (2011.01)
A61B 8/00 (2006.01)
A61B 8/08 (2006.01)

(52) U.S. Cl.
CPC ............. *G06T 7/0012* (2013.01); *A61B 8/4254* (2013.01); *A61B 8/5207* (2013.01); *A61B 8/5253* (2013.01); *G06T 11/206* (2013.01); *G06T 15/00* (2013.01); *G06T 19/00* (2013.01); *G06T 2210/41* (2013.01)

(58) Field of Classification Search
CPC combination set(s) only.
See application file for complete search history.

(56) References Cited

U.S. PATENT DOCUMENTS

2012/0262453 A1* 10/2012 Endo et al. .................... 345/419
2012/0262460 A1* 10/2012 Endo et al. .................... 345/441

FOREIGN PATENT DOCUMENTS

JP 2008-086742 A 4/2008

\* cited by examiner

*Primary Examiner* — Edward Martello
(74) *Attorney, Agent, or Firm* — Hazuki International, LLC

(57) ABSTRACT

An image processing apparatus includes a display controller. The display controller is configured to arrange a foreground image in a three-dimensional space and display, on a display device, the foreground image as an inspection status image representing an inspection status by an ultrasonic wave. The foreground image includes a linear image being as an image including a plurality of linear images that change in accordance with a status of a probe and connect the center of a circle and a circumference of the circle with each other, a probe image that is located at the center of the circle and has a shape of the probe, and a spherical image being as a spherical image that represents a range to which the ultrasonic wave output from the probe is applied and has a cross section as the circle.

14 Claims, 16 Drawing Sheets

IMAGE PROCESSING APPARATUS AND IMAGE PROCESSING METHOD

BACKGROUND

The present disclosure relates to an image processing apparatus and an image processing method, and more particularly to, an image processing apparatus and an image processing method that allow an operator who performs an ultrasonic inspection to easily grasp an inspection status of the ultrasonic inspection, for example.

In order to prevent omission of scanning at any inspected part in an ultrasonic inspection, there is proposed an ultrasonic inspection (diagnosis) apparatus that detects a position or a movement of a (ultrasonic) probe and expresses a track of the probe at an inspected part based on the position or the movement of the probe (for example, Japanese Patent Application Laid-open No. 2008-086742).

SUMMARY

In ultrasonic inspection apparatuses that perform ultrasonic inspections, a technique by which an operator who performs an ultrasonic inspection can easily grasp an inspection status of the ultrasonic inspection has been expected.

In view of the circumstances as described above, it is desirable for an operator who performs an ultrasonic inspection to easily grasp an inspection status of the ultrasonic inspection.

According to an embodiment of the present disclosure, there is provided an image processing apparatus including a display controller configured to arrange a foreground image in a three-dimensional space and display, on a display device, the foreground image as an inspection status image representing an inspection status by an ultrasonic wave, the foreground image including a linear image being as an image including a plurality of linear images that change in accordance with a status of a probe and connect the center of a circle and a circumference of the circle with each other, a probe image that is located at the center of the circle and has a shape of the probe, and a spherical image being as a spherical image that represents a range to which the ultrasonic wave output from the probe is applied and has a cross section as the circle.

According to another embodiment of the present disclosure, there is provided an image processing method including arranging a foreground image in a three-dimensional space and displaying, on a display device, the foreground image as an inspection status image representing an inspection status by an ultrasonic wave, the foreground image including a linear image being as an image including a plurality of linear images that change in accordance with a status of a probe and connect the center of a circle and a circumference of the circle with each other, a probe image that is located at the center of the circle and has a shape of the probe, and a spherical image being as a spherical image that represents a range to which the ultrasonic wave output from the probe is applied and has a cross section as the circle.

In the embodiments as described above, the foreground image including the linear image, the probe image, and the spherical image is arranged in the three-dimensional space and displayed as an inspection status image representing an inspection status by an ultrasonic wave, on the display device. The linear image is an image including a plurality of linear images that change in accordance with a status of the probe and connect the center of a circle and a circumference of the circle with each other. The probe image is located at the center of the circle and has a shape of the probe. The spherical image is a spherical image that represents a range to which the ultrasonic wave output from the probe is applied and has a cross section as the circle.

It should be noted that the image processing apparatus may be an independent apparatus or may be an internal block constituting one apparatus.

Further, when a computer is caused to execute a program, the computer can function as an image processing apparatus. A program causing the computer to function as an image processing apparatus can be provided by transmission via a transmission medium or recording on a recording medium.

According to the present disclosure, it is possible to grasp an inspection status of an ultrasonic inspection. In particular, an operator who performs an ultrasonic inspection can easily grasp an inspection status of the ultrasonic inspection.

These and other objects, features and advantages of the present disclosure will become more apparent in light of the following detailed description of best mode embodiments thereof, as illustrated in the accompanying drawings.

DETAILED DESCRIPTION OF EMBODIMENTS

Figure 1:
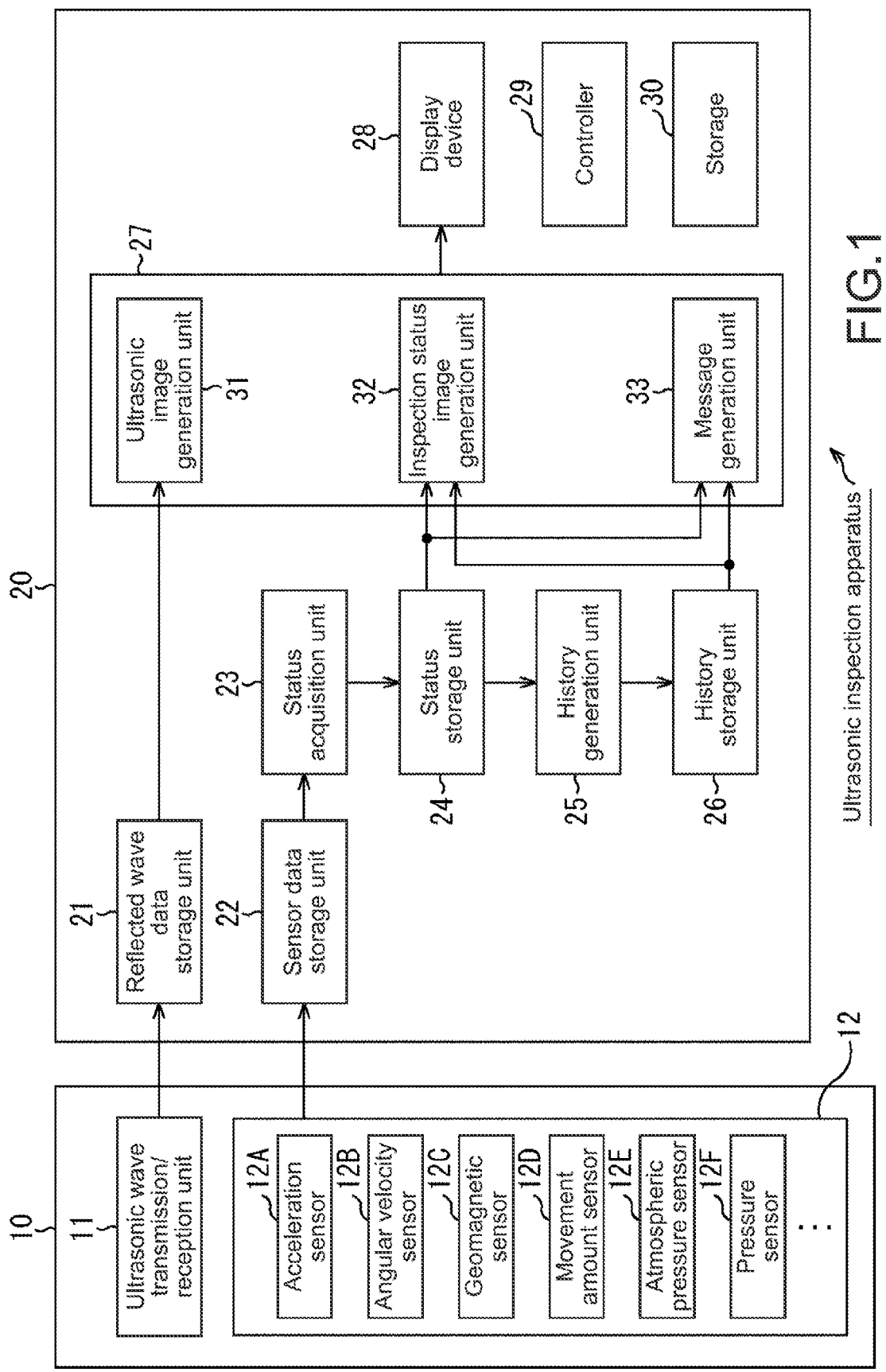
FIG. 1 is a block diagram showing a configuration example of an embodiment of an ultrasonic inspection apparatus to which an image processing apparatus according to an embodiment of the present disclosure is applied.

One Embodiment of Ultrasonic Inspection Apparatus to which One Embodiment of Present Disclosure is Applied FIG. 1 is a block diagram showing a configuration example of an embodiment of an ultrasonic inspection apparatus to which an image processing apparatus according to an embodiment of the present disclosure is applied.

The ultrasonic inspection apparatus is operated by an operator who performs an ultrasonic inspection. The ultrasonic inspection apparatus captures a cross-sectional image of each part such as abdomen of an inspection subject of an ultrasonic inspection by the use of an ultrasonic wave. The image captured with the ultrasonic inspection apparatus, that is, an ultrasonic image, is used in, for example, medical examinations by a doctor and the like.

It should be noted that the operator may be a third party other than the inspection subject, such as an engineer of the ultrasonic inspection, or may be the inspection subject himself/herself.

In FIG. 1, the ultrasonic inspection apparatus includes a probe 10 and a data processing unit 20.

The probe 10 is an ultrasonic probe to output an ultrasonic wave and to receive a reflected wave that come back by reflection of the ultrasonic wave on (the inside of the body of) the inspection subject. The probe 10 includes an ultrasonic wave transmission/reception unit 11 and a sensing unit 12.

The ultrasonic wave transmission/reception unit 11 is provided at a leading end of the probe 10, for example. The ultrasonic wave transmission/reception unit 11 generates and outputs an ultrasonic wave, receives a reflected wave of the ultrasonic wave, which is reflected on the inspection subject, and supplies reflected wave data indicating the intensity of the reflected wave to a reflected wave data storage unit 21 of the data processing unit 20.

The sensing unit 12 senses a physical amount that is necessary to detect the status of the probe 10.

Specifically, the sensing unit 12 includes an acceleration sensor 12A, an angular velocity sensor 12B, a geomagnetic sensor 12C, a movement amount sensor 12D, an atmospheric pressure sensor 12E, a pressure sensor 12F, and the like.

The acceleration sensor 12A detects an acceleration and an inclination of the probe 10, for example.

The angular velocity sensor 12B detects an angular velocity and a rotational angle of a rotation of the probe 10 in each direction of pitch, yaw, and roll.

The geomagnetic sensor 12C detects an orientation (direction) of the probe 10 with respect to a direction of geomagnetism, for example.

The movement amount (position) sensor 12D detects a movement amount of the probe 10 in a translation direction, for example.

The atmospheric pressure sensor 12E detects a position of the probe 10 in a height direction by atmospheric pressure, for example.

The pressure sensor 12F detects a pressure (contact pressure) at which the probe 10 presses an inspection subject when the probe 10 is put on the inspection subject.

The sensing unit 12 supplies data (sensor data) detected by the acceleration sensor 12A, the angular velocity sensor 12B, the geomagnetic sensor 12C, the movement amount sensor 12D, the atmospheric pressure sensor 12E, the pressure sensor 12F, and the like to a sensor data storage unit 22 of the data processing unit 20.

It should be noted that the sensing unit 12 can be provided with any sensors to sense a physical amount that is necessary to detect the status of the probe 10, such as a gyroscope sensor and a gravity sensor, in addition to the acceleration sensor 12A to the pressure sensor 12F.

The data processing unit 20 uses the reflected wave data or sensor data supplied from the probe 10 to generate an ultrasonic image or the like for display.

The data processing unit 20 includes the reflected wave data storage unit 21, the sensor data storage unit 22, a status acquisition unit 23, a status storage unit 24, a history generation unit 25, a history storage unit 26, a display controller 27, a display device 28, a controller 29, and a storage 30.

The reflected wave data storage unit 21 stores the reflected wave data supplied from the ultrasonic wave transmission/reception unit 11 of the probe 10.

The sensor data storage unit 22 stores the sensor data supplied from the sensing unit 12 of the probe 10.

The status acquisition unit 23 detects and acquires the status of the probe 10 at each time of day (timing at each predetermined interval) from the sensor data stored in the sensor data storage unit 22 and then supplies the status to the status storage unit 24.

Here, the status of the probe 10 includes a pressure (F) of the probe 10 that is put on the inspection subject, a position (Px, Py, Pz) of the probe 10, a direction (Yaw, Pitch, Roll) of the probe 10, a movement speed (Mx, My, Mz) in a translation direction of the probe 10, and the like.

The pressure (F) of the probe 10 is detected based on the sensor data of the pressure sensor 12F, for example.

The position (Px, Py, Pz) of the probe 10 is detected based on the sensor data of the movement amount sensor 12D and the acceleration sensor 12A, for example. Further, the position (Px, Py, Pz) of the probe 10 is represented in coordinates (x, y, z) of a three-dimensional coordinate system (hereinafter, referred to as probe coordinate system), for example. In the three-dimensional coordinate system, the position of the probe 10 that is put on an inspection subject in the last minute is set as the origin point, and the z axis is set as a direction of gravity.

The direction (Yaw, Pitch, Roll) of the probe 10 represents a posture of the probe 10. The direction (Yaw, Pitch, Roll) of the probe 10 is detected based on the sensor data of the acceleration sensor 12A, the geomagnetic sensor 12C, and a gyroscope sensor (not shown), for example. Further, the direction (Yaw, Pitch, Roll) of the probe 10 is represented by a rotational angle of the yaw direction, a rotational angle of the pitch direction, and a rotational angle of the roll direction, in a direction in which the ultrasonic wave is output from the probe 10 (ultrasonic wave output direction), for example.

The movement speed (Mx, My, Mz) of the probe 10 is detected based on the positions (Px, Py, Pz) of the probe 10 at a plurality of continuous times of day and based on the plurality of continuous times of day, for example.

It should be noted that the position (Px, Py, Pz) of the probe 10 is detected based on the sensor data of the movement amount sensor 12D and the acceleration sensor 12A and in addition, for example, the position (Px, Py, Pz) of the probe 10 at which a current ultrasonic image is captured (generated) can be detected by matching using ultrasonic images that have been generated until then in the ultrasonic image generation unit 31 that will be described later.

The status storage unit 24 stores a status of the probe 10 at each time of day, which is supplied from the status acquisition unit 23, in association with the time of day.

The history generation unit 25 generates a status history of the probe 10 from a time when the probe 10 is put on the inspection subject in the last minute to the moment, for example, using the status of the probe 10 that is stored in the status storage unit 24. Then, the history generation unit 25 supplies the status history to the history storage unit 26.

Here, the status history of the probe 10 includes a total time period (T) during which the probe 10 at each posture is put on the inspection subject, a movement path and a movement distance of the probe 10 from a time when the probe 10 is put on the inspection subject in the last minute to the moment, and the like.

The total time period (T) during which the probe 10 at each posture is put on the inspection subject is generated by totalizing times (inspection times) for each posture (direction) (Yaw, Pitch, Roll) of the probe 10 during which the probe 10 is put on the inspection subject at the posture, for example.

The movement path of the probe 10 is generated as a trajectory including the position (Px, Py, Pz) of the probe 10, and the movement distance of the probe 10 is generated from the position (Px, Py, Pz) of the probe 10.

The history storage unit 26 stores the status history of the probe 10, which is supplied from the history generation unit 25.

The display controller 27 performs display control to display an ultrasonic image, an inspection status image, and a predetermined message on the display device 28.

Specifically, the display controller 27 includes an ultrasonic image generation unit 31, an inspection status image generation unit 32, and a message generation unit 33.

The ultrasonic image generation unit 31 generates, as an ultrasonic image, an image in which the reflected wave data (the intensity of the reflected wave of the ultrasonic wave reflected on the inspection subject) stored in the reflected wave data storage unit 21 is considered as a pixel value (brightness), for example. Then, the ultrasonic image generation unit 31 supplies the image to the display device 28 for display.

Here, the ultrasonic wave transmission/reception unit 11 generates an ultrasonic wave and receives a reflected wave of the ultrasonic wave, and the ultrasonic image generation unit 31 generates an ultrasonic image by using the reflected wave data indicating the intensity of the reflected wave. Such processing corresponds to capturing of an ultrasonic image.

It should be noted that the ultrasonic image generation unit 31 can additionally generate, as an ultrasonic image, a cross-sectional image of a part such as abdomen by using the reflected wave data obtained by moving the probe 10 so as to go round the part.

The inspection status image generation unit 32 draws (generates) an inspection status image that represents the status of an inspection by the ultrasonic wave, by using the status of the probe 10 that is stored in the status storage unit 24 and the status history of the probe 10 that is stored in the history storage unit 26. Then, the inspection status image generation unit 32 supplies the inspection status image to the display device 28 for display.

For example, the message generation unit 33 generates a message for advice on an ultrasonic inspection method, by using the status of the probe 10 that is stored in the storage unit 24 and the status history of the probe 10 that is stored in the history storage unit 26. Then, the message generation unit 33 supplies the message to the display device 28 for display.

It should be noted that the display and non-display of the inspection status image or the message can be switched according to an operation of an operator, for example.

The display device 28 is constituted of an LCD (Liquid Crystal Display), an organic EL (Electro Luminescence) display, or the like. The display device 28 displays the ultrasonic image, the inspection status image, or the message according to the display control of the display controller 27.

The controller 29 controls the blocks that constitute the probe 10 and the blocks that constitute the data processing unit 20.

Further, the controller 29 sets (adjusts) a parameter of the probe 10 according to an operation of the operator, for example.

Here, examples of the parameter of the probe 10 include the type of the probe 10 (linear type, convex type, etc.), the number of piezoelectric elements that generate ultrasonic waves and receive reflected waves thereof in the probe 10, the frequency of an ultrasonic wave, the depth (to what depth the inspection is performed), a focus, a frame rate (frame rate in the case where an ultrasonic image is captured as a moving image), and the like. The controller 29 sets adjustable parameters (for example, frequency and focus of the ultrasonic wave) according to the operation of the operator.

The storage 30 associates the ultrasonic image generated in the ultrasonic image generation unit 31, the inspection status image generated in the inspection status image generation unit 32 when the ultrasonic image is generated, and the message generated in the message generation unit 33 with one another as necessary and then stores them.

It should be noted that in FIG. 1, the status of the probe 10 is detected using the sensor data that is output by the sensing unit 12 provided in the probe 10, but the status of the probe 10 can be detected by any other methods.

For example, the position of the probe 10 can be detected with use of a detection apparatus that detects a three-dimensional position of an object. As the detection apparatus that detects a three-dimensional position of an object, for example, there are a POLARIS (of an optical system) manufactured by NDI (Northern Digital Inc.), a medSAFE (of a magnetic system) manufactured by Ascension Technology Corporation, and the like.

Further, in FIG. 1, the display device 28 is included in the data processing unit 20, but the data processing unit 20 can be configured without including the display device 28.

Figure 2:
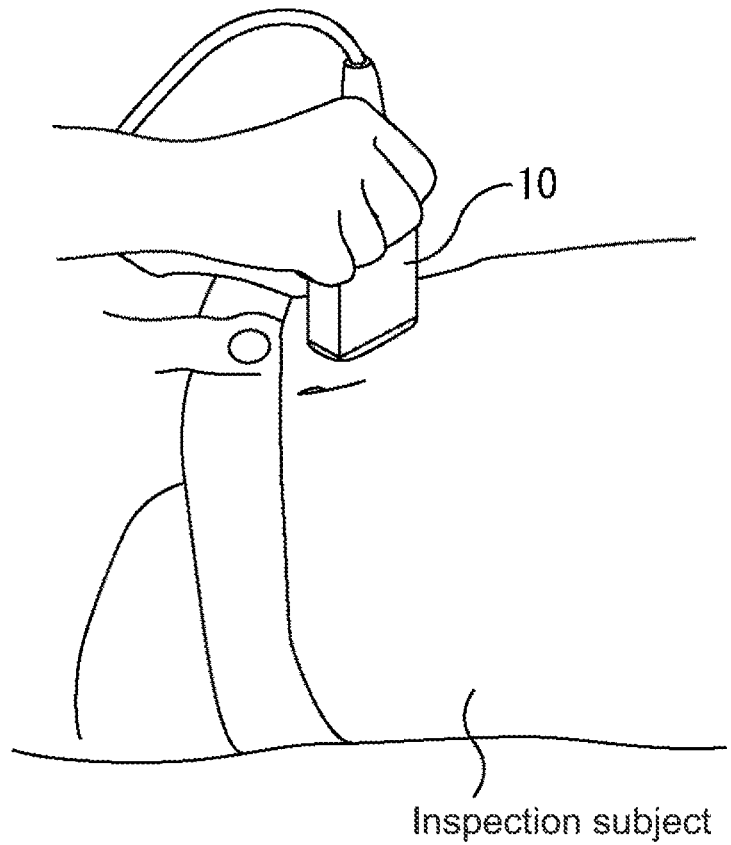
FIG. 2 is a diagram showing a state of the ultrasonic inspection.

FIG. 2 is a diagram showing a state of the ultrasonic inspection.

The ultrasonic inspection is performed by putting a part of the probe 10, at which an ultrasonic wave is output and a reflected wave is received, on a part whose ultrasonic image is intended to be obtained.

In FIG. 2, the probe 10 is being put on abdomen of an inspection subject lying down on his/her back.

Figure 3:
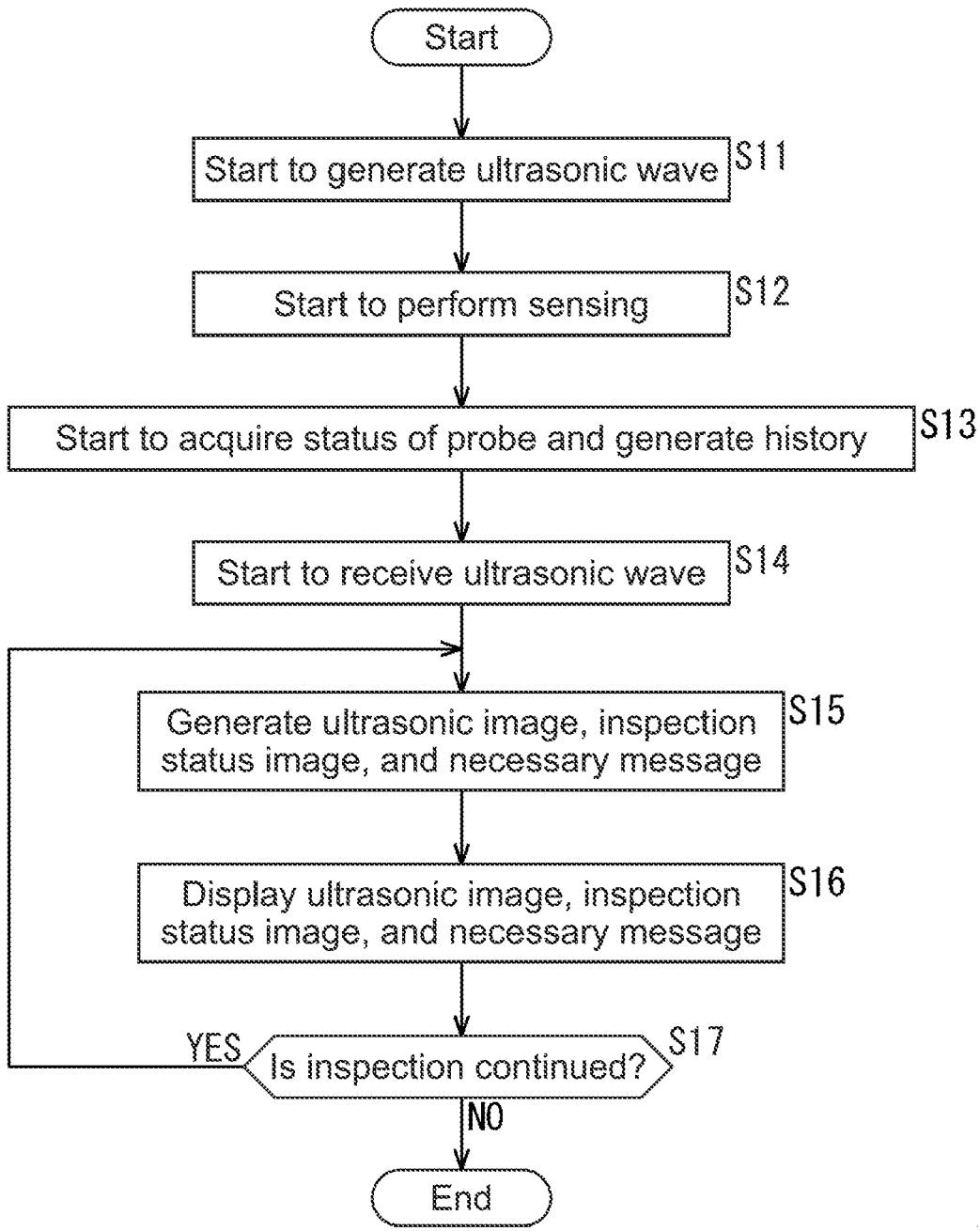
FIG. 3 is a flowchart for describing processing of the ultrasonic inspection apparatus.

FIG. 3 is a flowchart for describing processing of the ultrasonic inspection apparatus of FIG. 1.

In Step S11, the ultrasonic wave transmission/reception unit 11 starts to generate an ultrasonic wave according to an operation of an operator, for example. For example, the ultrasonic wave transmission/reception unit 11 generates a pulse-like ultrasonic wave at predetermined intervals and performs ultrasonic wave scanning in a predetermined direction.

In Step S12, the sensing unit 12 starts to sense a physical amount necessary to detect the status of the probe 10.

Sensor data obtained by the sensing of the sensing unit 12 is supplied to the sensor data storage unit 22 and then stored therein.

In Step S13, the status acquisition unit 23 starts to detect the status of the probe 10 by using the sensor data stored in the sensor data storage unit 22, and the history generation unit 25 starts to generate a status history of the probe 10 by using the status of the probe 10 that is detected by the status acquisition unit 23 (and stored in the status storage unit 24).

The status of the probe 10 that is detected by the status acquisition unit 23 is supplied to the status storage unit 24 and stored therein in association with a time of day. Further, the status history of the probe 10 that is generated in the history generation unit 25 is supplied to the history storage unit 26 and then stored therein.

In Step S14, the ultrasonic wave transmission/reception unit 11 starts to receive a reflected wave of the ultrasonic wave.

Reflected wave data indicating the intensity of the reflected wave received in the ultrasonic wave transmission/reception unit 11 is supplied to the reflected wave data storage unit 21 and stored therein.

In Step S15, the ultrasonic image generation unit 31 generates, as an ultrasonic image, an image in which the reflected wave data stored in the reflected wave data storage unit 21 is considered as a pixel value, for example.

Further, in Step S15, the inspection status image generation unit 32 generates an inspection status image by using the status of the probe 10 that is stored in the status storage unit 24 and the status history of the probe 10 that is stored in the history storage unit 26.

Furthermore, in Step S15, the message generation unit 33 generates a necessary message by using the status of the probe 10 that is stored in the status storage unit 24 and the status history of the probe 10 that is stored in the history storage unit 26.

In Step S16, the ultrasonic image generation unit 31 supplies the ultrasonic image to the display device 28 for display. In addition, in Step S16, the inspection status image generation unit 32 supplies the inspection status image to the display device 28 for display. Moreover, in Step S16, the message generation unit 33 supplies the necessary message to the display device 28 for display.

In Step S17, the controller 29 determines whether the ultrasonic inspection is continued or not.

In Step S17, in the case where it is determined that the ultrasonic inspection is continued, in other words, for example, in the case where the operator has not performed an operation of stopping the ultrasonic inspection, the processing returns to Step S15 and the same processing is repeated from Step S15.

Alternatively, in the case where it is determined in Step S17 that the ultrasonic inspection is not continued, in other words, for example, in the case where the operator has performed an operation of stopping the ultrasonic inspection, the processing is terminated.

Figure 4:
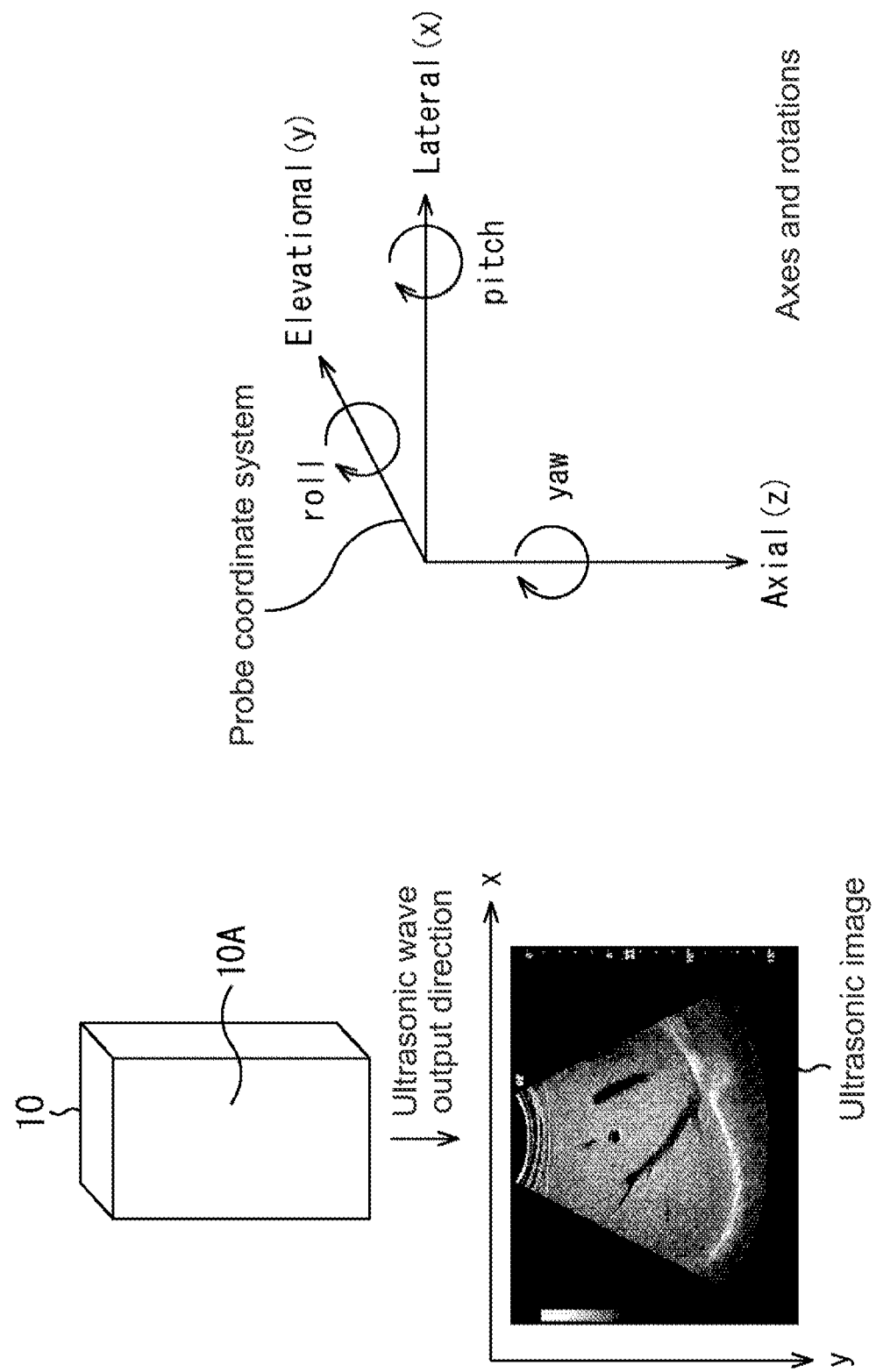
FIG. 4 is a diagram for describing a posture of a probe.

FIG. 4 is a diagram for describing a posture of the probe 10.

The posture of the probe 10 is represented by the direction (Yaw, Pitch, Roll) of the probe 10. The direction (Yaw, Pitch, Roll) of the probe 10 is represented by a rotational angle of the yaw direction, a rotational angle of the pitch direction, and a rotational angle of the roll direction, in a direction in which the ultrasonic wave is output from the probe 10 (ultrasonic wave output direction).

It is assumed that the position of the probe 10 when the probe 10 is put on the inspection subject in the last minute is set as the origin point, and a three-dimensional coordinate system with the z axis being a direction of gravity is set as a probe coordinate system. In this case, the rotational angle of the pitch direction represents a rotational angle about an x axis of the probe coordinate system, the rotational angle of the roll direction represents a rotational angle about a y axis of the probe coordinate system, and the rotational angle of the yaw direction represents a rotational angle about the z axis of the probe coordinate system.

Here, in order to simplify the description, it is assumed that the probe 10 has a shape of a cuboid. The cuboid serves as the probe 10 in a state in which the ultrasonic wave output direction coincides with the z axis of the probe coordinate system. The status of the physical appearance of the probe 10 is identical between a case where one surface of the cuboid that is parallel to the ultrasonic wave output direction, that is, a front surface 10A, faces the front as shown in FIG. 4, for example, and the other case where the front surface 10A rotates by 180 degrees about the z axis and faces the opposite side. However, the two cases are different from each other in the rotational angle of the yaw direction, and thus different from each other in the posture of the probe 10.

It should be noted that the x axis and the y axis of the probe coordinate system can be determined from directions orthogonal to the z axis by any method. Further, although FIG. 4 shows an x axis and a y axis of an ultrasonic image coordinate system, the x axis and the y axis of the ultrasonic image coordinate system represent a lateral direction and a longitudinal direction of the ultrasonic image, respectively, which differ from the x axis and the y axis of the probe coordinate system.

(Inspection Status Image)

Hereinafter, display examples of the inspection status image that is generated (drawn) in the inspection status image generation unit 32 will be described.

Figure 5:
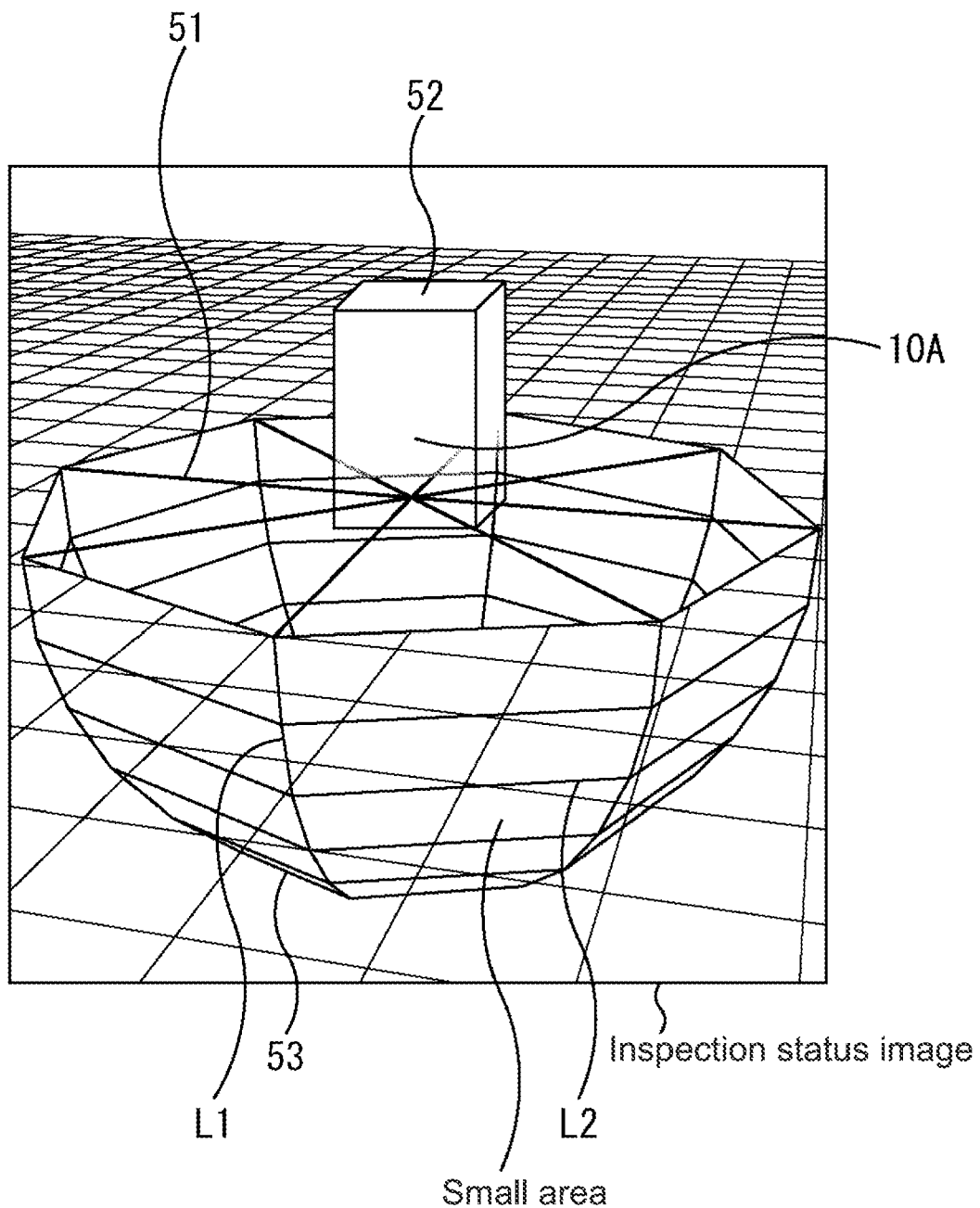
FIG. 5 is a diagram showing a display example of an inspection status image obtained when the probe is put on an inspection subject.

FIG. 5 is a diagram showing a display example of the inspection status image obtained when the probe 10 is put on an inspection subject.

For example, the inspection status image is an image in which a foreground image serving as a linear image 51, a probe image 52, and a spherical image 53 is arranged in a virtual three-dimensional space serving as a background image.

The linear image 51 includes a plurality of linear images that connect the center of a predetermined circle and a circumference of the predetermined circle. In FIG. 5, eight lines are drawn as a plurality of lines that connect the center of a predetermined circle and a circumference of the predetermined circle.

The linear image 51 changes in accordance with the status of the probe 10 as will be described later.

The probe image 52 is an image in the shape of the probe 10. In FIG. 5, (an image of) a cuboid is adopted as the probe image 52.

A circle with the position of the probe image 52 being as the center is adopted as the predetermined circle used when the linear image 51 is drawn. Therefore, the probe image 52 is positioned at the center of the predetermined circle used when the linear image 51 is drawn.

It should be noted that the cuboid as the probe image 52 can be drawn such that a part from which an ultrasonic wave is output is visually recognized. In FIG. 5, a part of the cuboid as the probe image 52, from which an ultrasonic wave is output, is drawn in a translucent manner.

The probe image 52 changes in accordance with the status of the probe 10.

For example, as shown in FIG. 2, in the case where the probe 10 is being put on the inspection subject lying down such that the ultrasonic wave output direction is (substantially) perpendicular to the inspection subject, the probe image 52 is drawn such that the ultrasonic wave output direction is perpendicular to the predetermined circle used when the linear image 51 is drawn.

Then, for example, when the probe 10 is inclined, the probe image 52 is inclined similarly. In other words, the probe image 52 is redrawn to show a state in which the probe image 52 is inclined similarly to the probe 10.

It should be noted that in the case of adopting a cuboid or the like shown in FIG. 5 as the probe image 52, it is difficult to distinguish the case where the front surface 10A of the probe 10 faces the front from the case where the front surface 10A rotates by 180 degrees about the z axis and faces the opposite side, as described with reference to FIG. 4.

In this regard, on a surface of the cuboid as the probe image 52, which corresponds to the front surface 10A of the probe 10, a mark or the like indicating that the surface corresponds to the front surface 10A can be drawn. In this case, the operator can easily grasp a direction in which the front surface 10A of the probe 10 faces.

The spherical image 53 is a (hemi)spherical image representing a range to which an ultrasonic wave output from the probe 10 is applied. The spherical image 53 has a cross section as the predetermined circle used when the linear image 51 is drawn.

The center of the hemisphere as the spherical image 53 is the center of the predetermined circle used when the linear image 51 is drawn, that is, the position where the probe image 52 is positioned. Therefore, by the spherical image 53, the operator can imagine the range inside of the body of the inspection subject, to which an ultrasonic wave output from the probe 10 is applied, the probe 10 being put on the body surface of the inspection subject.

In order to ensure the visibility, the inside of the hemisphere as the spherical image 53 is a hollow so as to see the inside (back side) on the depth side of the hemisphere.

It should be noted that in FIG. 5, a point of view is present on an upper side on the front of the hemisphere as the spherical image 53. In terms of ensuring the visibility of the inside on the depth side of the hemisphere as the spherical image 53 as much as possible without changing the point of view, the surface (spherical surface) of the hemisphere as the spherical image 53 is drawn in a transparent (translucent) manner.

Here, in FIG. 5, the cross section of the hemisphere as the spherical image 53, that is, the predetermined circle used when the linear image 51 is drawn, is closely analogous to a regular octagon.

Further, in FIG. 5, the spherical image 53 is drawn in wireframe. The surface of the hemisphere as the spherical image 53 is sectioned into small areas by lines L1 and L2 that are drawn in a grid form and serve as wireframe.

In other words, the surface of the hemisphere as the spherical image 53 is sectioned into small areas each having a substantially rectangular shape by the lines L1 and the lines L2. The lines L1 connect, along with the surface of the hemisphere, opposed vertices of cross sections of the hemisphere that are each closely analogous to a regular octagon. The lines L2 are obtained by intersections of a plurality of flat surfaces and the hemisphere. The plurality of flat surfaces are parallel to the cross section of the hemisphere and arranged at regular intervals.

It should be noted that when the probe 10 is put on the inspection subject in a state where the inspection subject stands up, the linear image 51, the probe image 52, and the spherical image 53 that serve as the foreground image can be drawn in a 90-degrees rotated state from the state of FIG. 2. In this case, the operator can easily imagine that an ultrasonic inspection for the inspection subject who is standing up is being performed.

Figure 6:
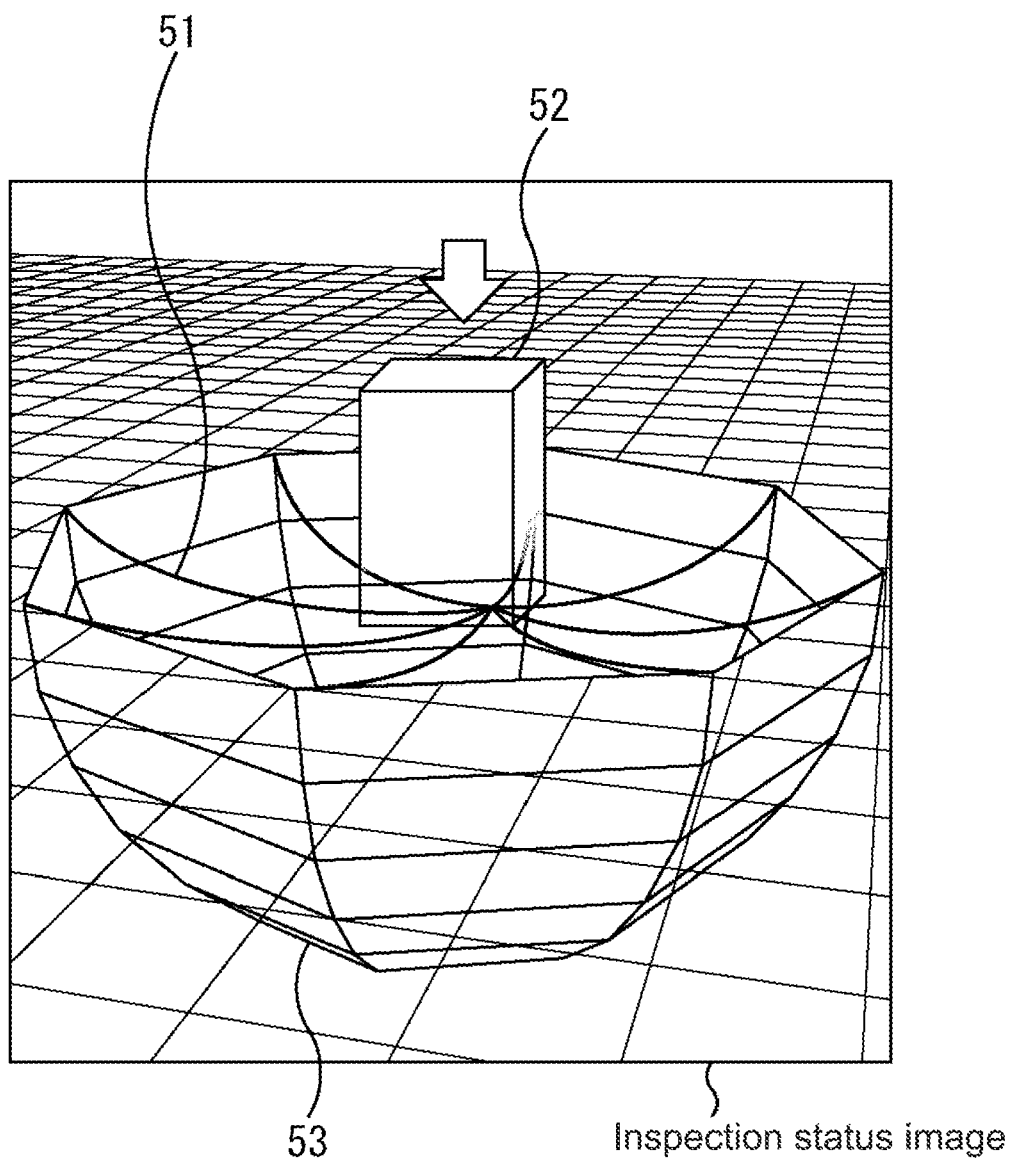
FIG. 6 is a diagram showing another display example of the inspection status image obtained when the probe is being pressed against the inspection subject with a certain amount of force.

FIG. 6 is a diagram showing another display example of the inspection status image obtained when the probe 10 is being pressed against the inspection subject with a certain amount of force.

It should be noted that in FIG. 6, for simple description, the position of the probe 10 is not transferred, and the posture thereof is not changed.

In the case where the probe 10 is being pressed against the inspection subject, the plurality of lines serving as the linear image 51 are deflected in accordance with a pressure of the probe 10 that is being pressed against the inspection subject.

In other words, the plurality of lines serving as the linear image 51 are drawn so as to be deflected in accordance with the pressure of the probe 10 that is being pressed against the inspection subject.

By the deflection corresponding to the pressure of the probe 10 that is being pressed against the inspection subject, which is given to the plurality of lines serving as the linear image 51, the operator can visually recognize the amount of the pressure of the probe 10.

It should be noted that as to the plurality of lines serving as the linear image 51, the deflection can be given thereto and the color or thickness thereof can be changed, in accordance with the pressure of the probe 10 that is being pressed against the inspection subject.

For example, in the case where the pressure of the probe 10 that is being pressed against the inspection subject becomes stronger, the color or thickness of the plurality of lines serving as the linear image 51 can be changed in order that the operator can imagine that the pressure of the probe 10 becomes stronger. For example, the plurality of lines serving as the linear image 51 can be changed in color from a light red color to a deep red color or changed in thickness from a thick line to a thin line.

Further, in the case where the pressure of the probe 10 becomes stronger, the plurality of lines serving as the linear image 51 can be changed in thickness from a thin line to a thick line. When the pressure of the probe 10 is strong and the plurality of lines serving as the linear image 51 are drawn in a thick line, an impression that the probe 10 is hard to press any more can be given to the operator.

Figure 7:
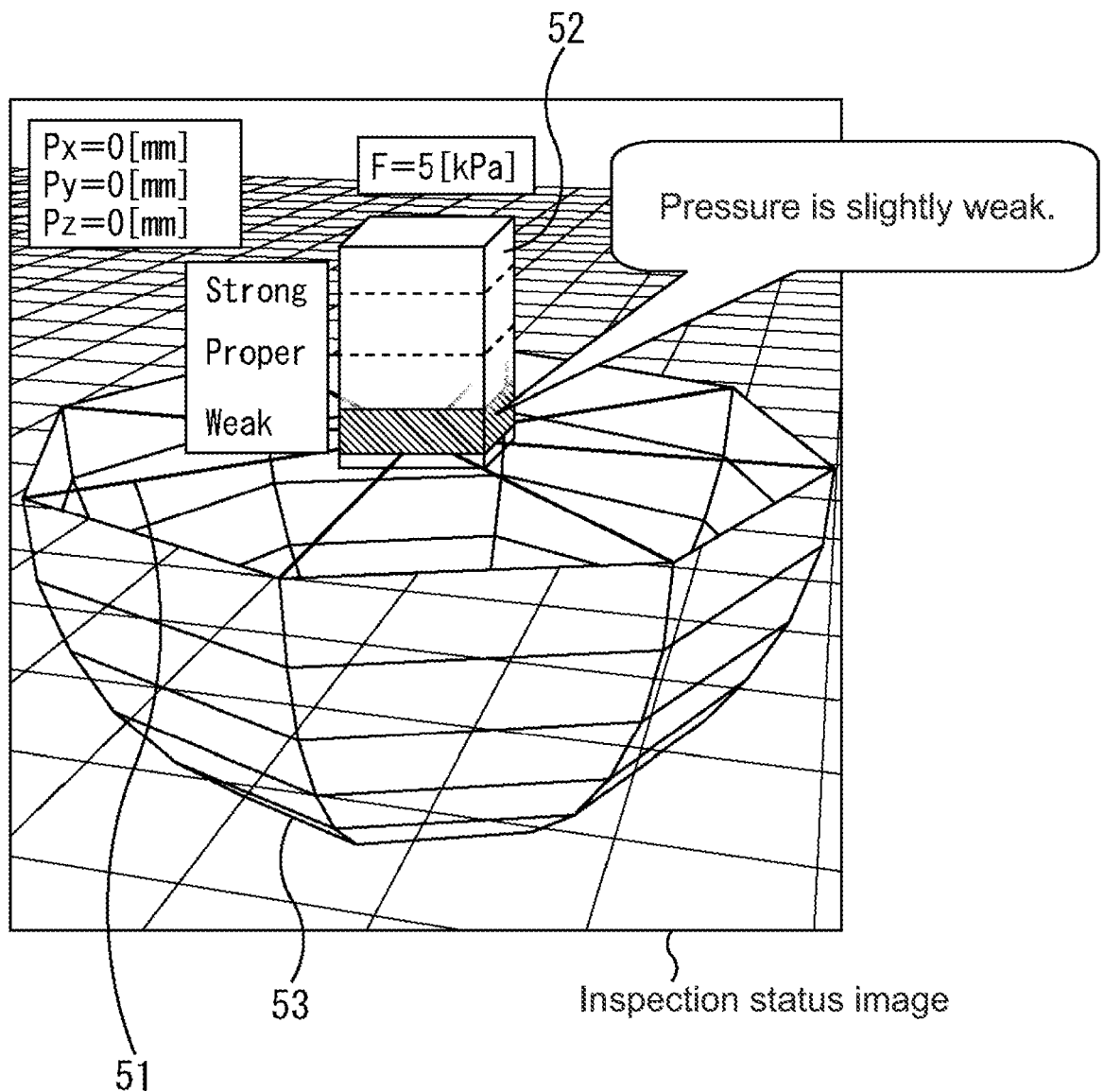
FIG. 7 is a diagram showing another display example of the inspection status image obtained when the probe is being pressed against the inspection subject with a certain amount of force.

FIG. 7 is a diagram showing another display example of the inspection status image obtained when the probe 10 is being pressed against the inspection subject with a certain amount of force.

It should be noted that also in FIG. 7, the position of the probe 10 is not transferred, and the posture thereof is not changed.

In FIG. 7, the probe image 52 functions as a level meter that indicates the pressure of the probe 10.

Specifically, in FIG. 7, the color or brightness of the cuboid as the probe image 52 is changed in a vertical direction from the bottom of the cuboid in accordance with the pressure of the probe 10 that is being pressed against the inspection subject.

As a result, the color or brightness of the cuboid as the probe image 52 is changed from the bottom of the cuboid in accordance with the pressure of the probe 10 such that a bar graph expands or contracts. In other words, as the pressure of the probe 10 becomes stronger, the color or brightness of the cuboid as the probe image 52 changes such that a bar graph expands.

Thus, the operator can visually recognize the amount of the pressure of the probe 10.

It should be noted that in FIG. 7, the probe image 52 that functions as a level meter of a pressure is provided with marks as a scale of the level meter. The marks represent that the pressure of the probe 10 is too weak (Weak), proper (Proper), and too strong (Strong).

With those marks, the operator can determine whether the pressure of the probe 10 is proper or not.

Further, in FIG. 7, the pressure of the probe 10 is weak (too weak). Therefore, a message for advice on an inspection method for an ultrasonic inspection, "Pressure is slightly weak", is generated in the message generation unit 33 and displayed.

As to whether the pressure of the probe 10 is proper or not, for example, a pressure database in which a proper pressure for each part that is subjected to the ultrasonic inspection is registered is stored in the message generation unit 33, and a part that is subjected to the ultrasonic inspection is input by the operator. Thus, whether the pressure of the probe 10 is proper or not can be determined with reference to the pressure database in the message generation unit 33.

Here, in FIG. 7, the indication of "F=5 [kPa]" represents a specific numerical value of the pressure of the probe 10 (pressure at which the probe 10 is pressed against the inspection subject).

Further, in FIG. 7, the indications of "Px=0 [mm]", "Py=0 [mm]", and "Pz=0 [mm]" represent the position (Px, Py, Pz) of the probe 10 (coordinates of the probe coordinate system).

Using the status of the probe 10 that is stored in the status storage unit 24, the display controller 27 can display a specific numerical value of the pressure of the probe 10 and the position (Px, Py, Pz) of the probe 10 as described above.

Figure 8:
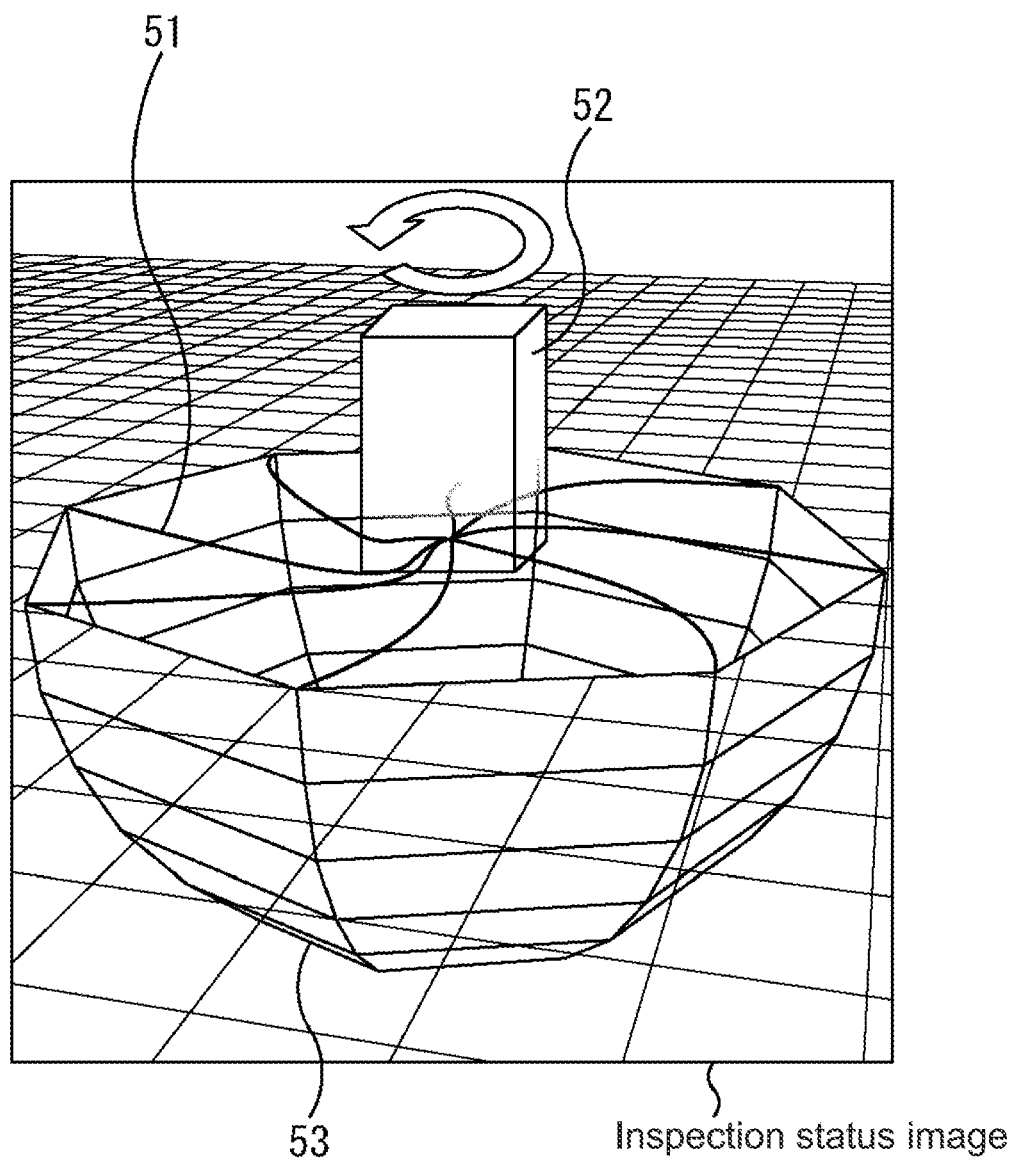
FIG. 8 is a diagram showing another display example of the inspection status image obtained when the probe is rotated about an ultrasonic wave output direction while being pressed against the inspection subject.

FIG. 8 is a diagram showing another display example of the inspection status image obtained when the probe 10 is rotated about the ultrasonic wave output direction while being pressed against the inspection subject.

It should be noted that in FIG. 8, for simple description, the position of the probe 10 is not transferred, and the pressure thereof is not changed.

In the case where the probe 10 is rotated about the ultrasonic wave output direction while being pressed against the inspection subject, that is, the probe 10 is twisted, the plurality of lines serving as the linear image 51 are twisted in accordance with an amount of the twist of the probe 10.

Specifically, the plurality of lines serving as the linear image 51 are drawn such that the twist occurs in accordance with an amount of the twist of the probe 10.

The twist corresponding to the amount of the twist of the probe 10 is added to the plurality of lines serving as the linear image 51. Thus, the operator can visually recognize the amount of the twist of the probe 10.

It should be noted that as to the plurality of lines serving as the linear image 51, the twist can be added thereto and the color or thickness thereof can be changed, in accordance with the amount of the twist of the probe 10.

The inspection status image generation unit 32 recognizes the amount of the twist of the probe 10 based on the posture of the probe 10 (the direction (Yaw, Pitch, Roll) of the probe 10). Then, the inspection status image generation unit 32 redraws the plurality of lines serving as the linear image 51 that are twisted in accordance with the amount of the twist of the probe 10.

Figure 9:
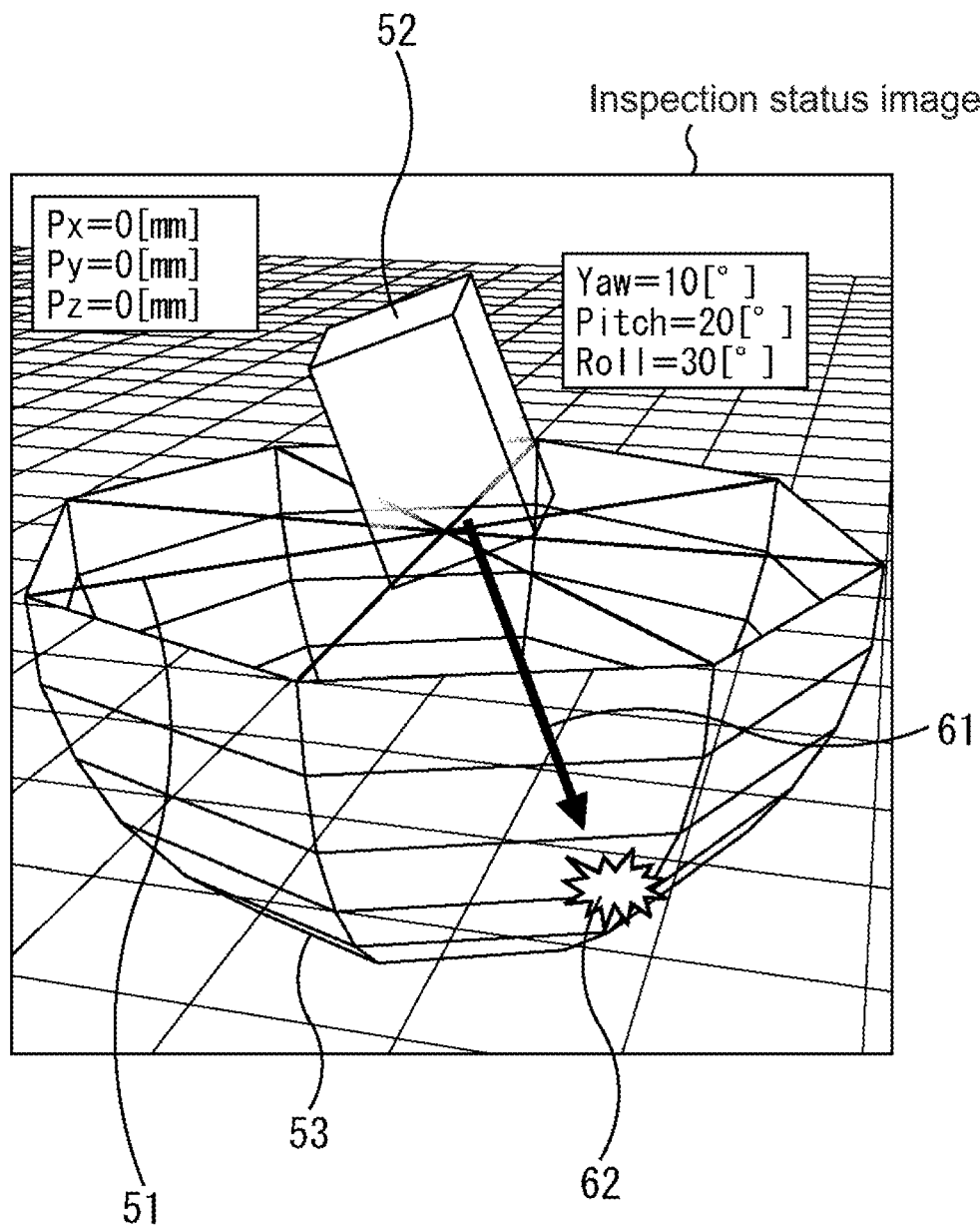
FIG. 9 is a diagram showing another display example of the inspection status image in which a direction image is drawn as a foreground image in addition to a linear image, a probe image, and a spherical image.

FIG. 9 is a diagram showing another display example of the inspection status image in which a direction image is drawn as the foreground image in addition to the linear image 51, the probe image 52, and the spherical image 53.

It should be noted that in FIG. 9, for simple description, the position of the probe 10 is not transferred, and the pressure thereof is not changed.

The direction image is an image indicating the ultrasonic wave output direction (direction in which the ultrasonic wave is output from the probe 10). In FIG. 9, as the direction image, a direction arrow image 61 and a direction point image 62 are drawn.

The direction arrow image 61 is an image of an arrow extending in the ultrasonic wave output direction with the center of the hemisphere as the spherical image 53 (center of the predetermined circle used when the linear image 51 is drawn) being as a starting point.

The inspection status image generation unit 32 recognizes the direction (Yaw, Pitch, Roll) of the probe 10 as the ultrasonic wave output direction and draws, as the direction arrow image 61, an image of an arrow extending in the ultrasonic wave output direction from the center of the hemisphere as the spherical image 53.

The direction point image 62 is an image that is drawn at an intersection between a line extending in the ultrasonic wave output direction from the center of the hemisphere as the spherical image 53 and the surface of the hemisphere as the spherical image 53 and that causes the operator to imagine that a beam is applied to the intersection.

The inspection status image generation unit 32 detects the intersection between the line extending in the ultrasonic wave output direction from the center of the hemisphere as the spherical image 53 and the surface of the hemisphere as the spherical image 53 and draws the direction point image 62 at the position of the intersection.

With the direction arrow image 61 and the direction point image 62 as the direction image, the operator can easily grasp the direction in which the ultrasonic inspection is performed (direction in which the ultrasonic wave is applied).

Here, in FIG. 9, the indications of "Px=0 [mm]", "Py=0 [mm]", and "Pz=0 [mm]" represent the position (Px, Py, Pz) of the probe 10 as described with reference to FIG. 7.

Further, the indications of the "Yaw=10 [°]", "Pitch=20 [°]", and "Roll=30 [°]" represent the posture of the probe 10 (the direction (Yaw, Pitch, Roll) of the probe 10).

Using the status of the probe 10 that is stored in the status storage unit 24, the display controller 27 can display the position (Px, Py, Pz) of the probe 10 and the direction (Yaw, Pitch, Roll) of the probe 10 as described above.

It should be noted that FIG. 9 shows both the direction arrow image 61 and the direction point image 62 that serve as the direction image, but only one of the direction arrow image 61 and the direction point image 62 can be displayed as the direction image.

Further, the direction point image 62 can be blinked.

Furthermore, a display status of the direction arrow image 61 and that of the direction point image 62 can be changed in accordance with the intensity, frequency, or the like of the ultrasonic wave that is output from the probe 10.

For example, the arrow as the direction arrow image 61 can be made thicker as the intensity of the ultrasonic wave that is output from the probe 10 becomes stronger. In this case, with the direction arrow image 61, the operator can easily grasp the level of the intensity of the ultrasonic wave that is output from the probe 10.

In addition, for example, the direction point image 62 can be blinked at higher speed as the frequency of the ultrasonic wave that is output from the probe 10 becomes higher.

Figure 10:
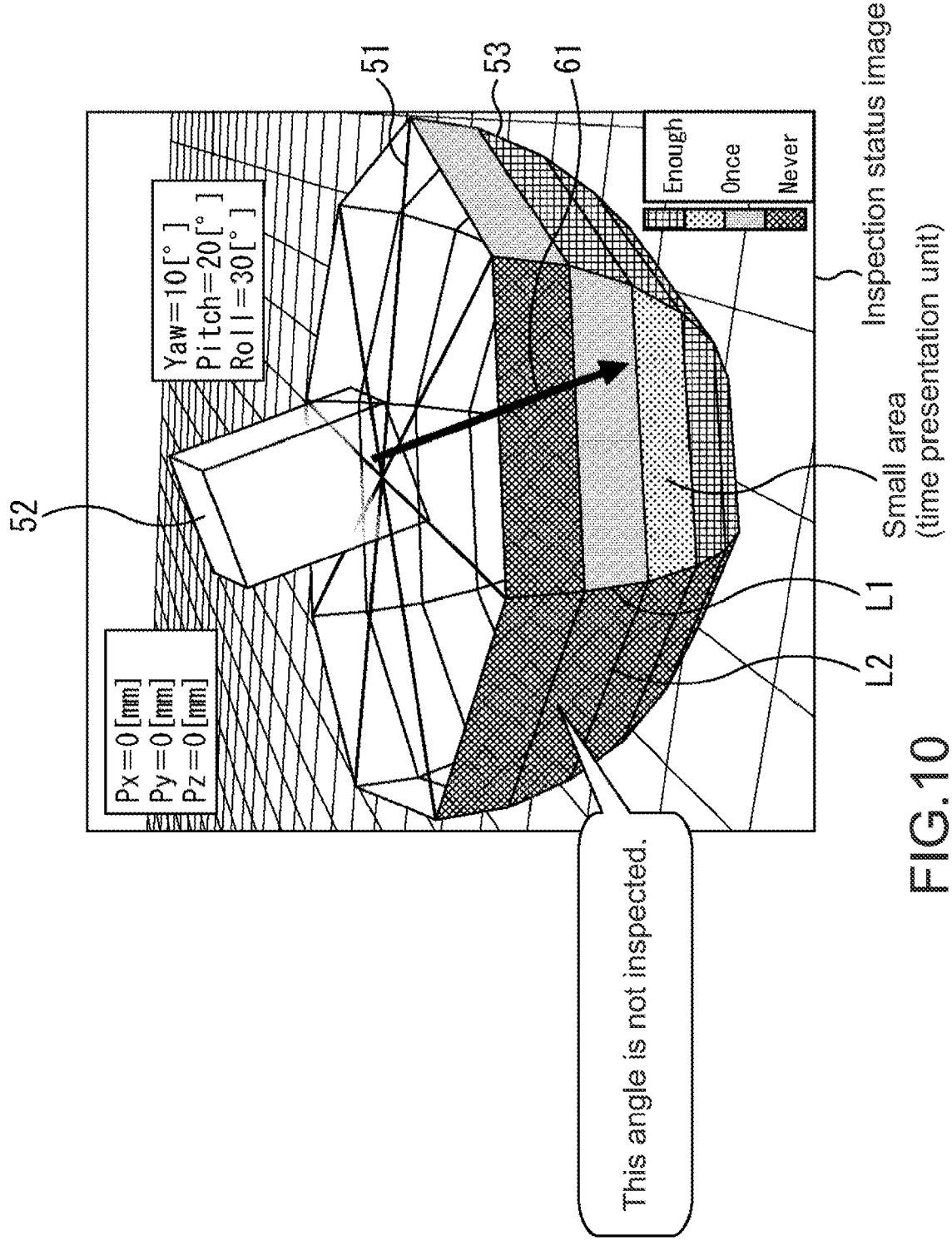
FIG. 10 is a diagram showing another display example of the inspection status image in which a texture of the spherical image is changed in accordance with an inspection time period of the ultrasonic inspection.

FIG. 10 is a diagram showing another display example of the inspection status image in which a texture of the spherical image 53 is changed in accordance with an inspection time period of the ultrasonic inspection.

It should be noted that in FIG. 10, for simple description, the position of the probe 10 is not transferred, and the pressure thereof is not changed.

In accordance with the inspection time period of the ultrasonic inspection in a direction from the center of the hemisphere as the spherical image 53 toward a predetermined position on the surface of the hemisphere, the inspection status image generation unit 32 can change the texture of the predetermined position.

Specifically, the inspection status image generation unit 32 sets the small areas, by which the surface of the hemisphere as the spherical image 53 is sectioned and which have been described with reference to FIG. 5, to be units for presenting the inspection time period of the ultrasonic inspection (time presentation unit). The inspection status image generation unit 32 changes the texture of each time presentation unit in accordance with an integration value of time periods during which the ultrasonic wave is applied to the time presentation unit.

In this case, the operator can easily grasp a direction in which the ultrasonic inspection is not performed (in which the ultrasonic wave is not applied) (when viewed from the center of the hemisphere as the spherical image 53, that is, from the position of the probe 10) or a direction in which the ultrasonic inspection is not sufficiently performed (in which a reflected wave of the ultrasonic wave is not sufficiently received).

Here, in the inspection status image generation unit 32, the integration value of the time period during which the ultrasonic wave is applied to the time presentation unit is obtained using the status history of the probe 10.

It should be noted that in FIG. 10, the texture of the time presentation unit is drawn so as to distinguish at least a direction in which the ultrasonic wave has never been applied (in which the inspection time period of the ultrasonic inspection is 0) (Never), a direction in which the ultrasonic wave has been applied but the application of the ultrasonic wave is not sufficient (in which the inspection time period is insufficient) (Once), and a direction in which the ultrasonic wave is sufficiently applied (in which the inspection time period is enough) (Enough).

Further, in FIG. 10, in the message generation unit 33, a message for advising the operator to perform an ultrasonic inspection (of a time presentation unit) in a direction in which the ultrasonic wave has not been applied, "This angle is not inspected", is generated and displayed with a speech balloon pointing to a time presentation unit in a direction in which the ultrasonic wave has not been applied.

Additionally, in FIG. 10, the indications of "Px=0 [mm]", "Py=0 [mm]", and "Pz=0 [mm]" and the indications of "Yaw=10 [°]", "Pitch=20 [°]", and "Roll=30 [°]" represent the position (Px, Py, Pz) of the probe 10 and the posture of the probe 10 (the direction (Yaw, Pitch, Roll) of the probe 10), as in the case of FIG. 9.

Here, in the case where an inspection subject who has been subjected to the ultrasonic inspection in the past is subjected to an ultrasonic inspection for the same part as that have been subjected to the past ultrasonic inspection, matching is performed in the status acquisition unit 23 between an ultrasonic image obtained in the past ultrasonic inspection and an ultrasonic image obtained in the ultrasonic inspection in this time. Then, for example, using the probe coordinate system used in the past ultrasonic inspection, the status of the probe 10 in the ultrasonic inspection in this time can be detected.

In this case, in the inspection status image generation unit 32, in accordance with an inspection time period obtained by integrating time periods from the past ultrasonic inspection to the ultrasonic inspection in this time, the texture of the time presentation unit can be changed.

Figure 11:
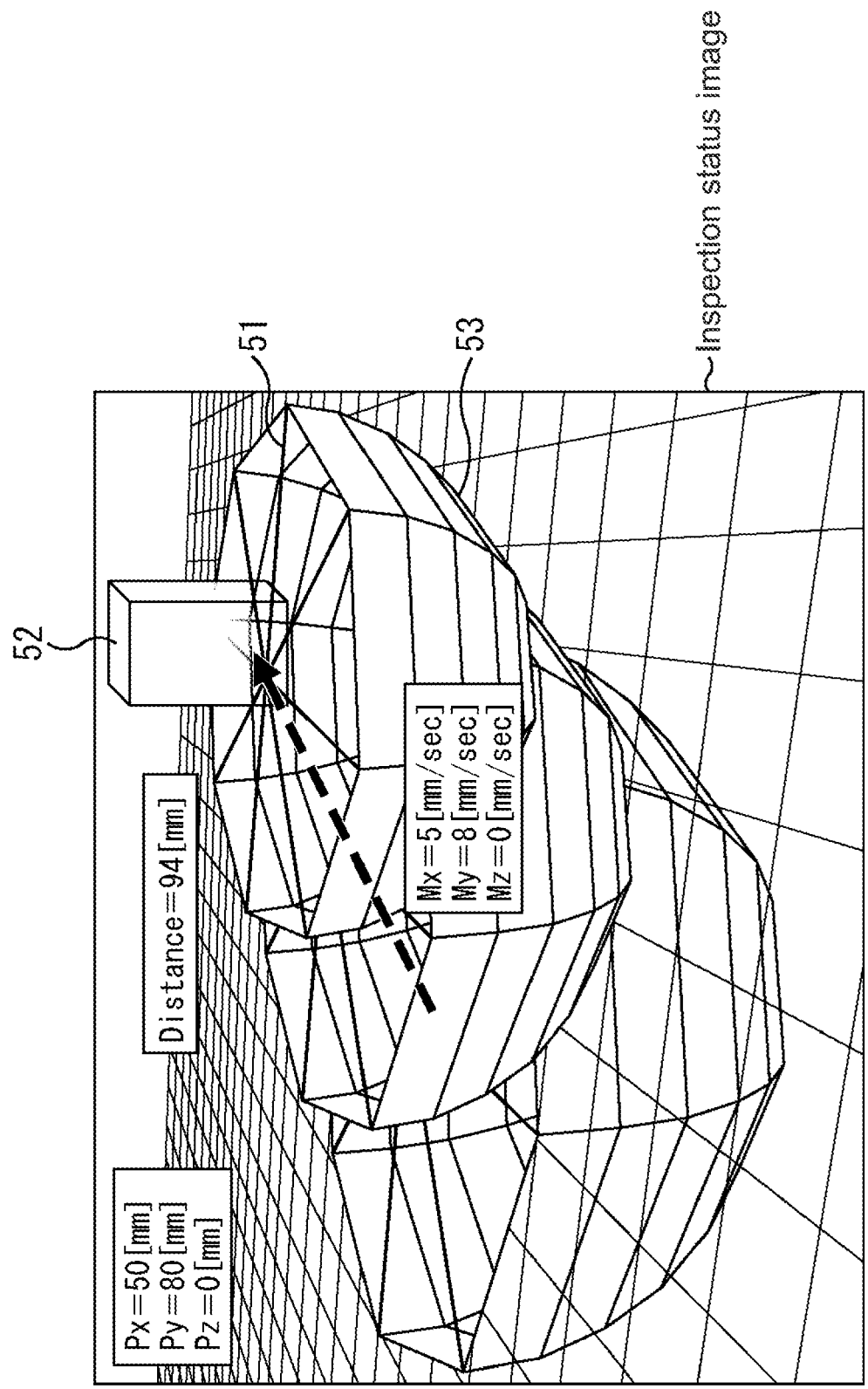
FIG. 11 is a diagram showing another display example of the inspection status image in which the foreground image that moves along with the movement of the probe within a three-dimensional space as a background image is drawn.

FIG. 11 is a diagram showing another display example of the inspection status image in which the foreground image that moves along with the movement of the probe 10 within a three-dimensional space as the background image is drawn.

It should be noted that in FIG. 11, for simple description, the posture and the pressure of the probe 10 are not changed.

FIG. 11 shows a display example of the inspection status image obtained when the operator moves the probe 10 from the front side to the deep side.

In the case where the operator moves the probe 10, the inspection status image generation unit 32 moves the linear image 51, the probe image 52, and the spherical image 53 as the foreground image within the three-dimensional space as the background image according to the movement of the probe 10.

Specifically, the inspection status image generation unit 32 draws and displays an inspection status image in which the foreground image is arranged at (a position corresponding to) a current position of the probe 10 being moved, within the three-dimensional space as the background image.

Here, when the foreground image is moved within the three-dimensional space, as shown in FIG. 11, the inspection status image generation unit 32 can also draw the foreground images at (positions corresponding to) one or more past positions of the probe 10 being moved, in addition to the current position of the probe 10 being moved, within the three-dimensional space as the background image.

In FIG. 11, the foreground images are drawn at two past positions of the probe 10 being moved, in addition to the current position of the probe 10 being moved.

The inspection status image generation unit 32 can determine intervals (crude density) between the positions at which the foreground images are drawn, in accordance with a speed at which the probe 10 is moved.

For example, at intervals at which a moving speed of the probe 10 is fast, positions at which the foreground images are drawn are roughly determined. At intervals at which the moving speed of the probe 10 is slow, the positions at which the foreground images are drawn are densely determined.

In this case, the operator can visually recognize the moving speed of the probe 10.

It should be noted that the foreground images drawn at the past positions can be merely deleted after the lapse of a predetermined period of time or can be set to increase the degree of transparency along with the lapse of time and eventually deleted, for example.

Further, when the foreground images are drawn, a foreground image located on the front side within the three-dimensional space is drawn in a large size, and a foreground image located on the deep side within the three-dimensional space is drawn in a small size so that the operator has a sense of perspective.

Here, in FIG. 11, the indications of "Px=50 [mm]", "Py=80 [mm]", and "Pz=0 [mm]" represent the position (Px, Py, Pz) of the probe 10 as described with reference to FIG. 7.

Further, the indications of "Mx=5 [mm/sec]", "My=8 [mm/sec]", and "Mz=0 [mm/sec]" represent the movement speed (Mx, My, Mz) in the translation direction of the probe 10.

Additionally, the indication of "Distance=94 [mm]" represents a movement distance of the probe 10.

Using the status of the probe 10 that is stored in the status storage unit 24, the display controller 27 can display the position (Px, Py, Pz) of the probe 10 and the movement speed (Mx, My, Mz) of the probe 10. Further, using the status history of the probe 10 that is stored in the history storage unit 26, the display controller 27 can display the movement distance of the probe 10.

Further, in FIG. 11, (an image of) an arrow indicated by a dotted line is a transfer path image representing a transfer path of the probe 10. The inspection status image generation unit 32 can draw the transfer path image by using the status history of the probe 10 that is stored in the history storage unit 26.

Hereinafter, with reference to FIGS. 12 to 16, an inspection status image in which a rotation information image is drawn in addition to the linear image 51, the probe image 52, and the spherical image 53 as the foreground image will be described.

It should be noted that in the following description, for simple description, the position of the probe 10 is not transferred, and the pressure thereof is not changed.

The inspection status image generation unit 32 can draw an image representing rotation information on a rotation of the probe 10, as a rotation information image in the foreground image. In this case, the rotation information on the rotation of the probe 10 is obtained when the probe 10 is rotated about the ultrasonic wave output direction while keeping a state directed from the center of the hemisphere as the spherical image 53 to a predetermined position on the surface of the hemisphere.

Figure 12:
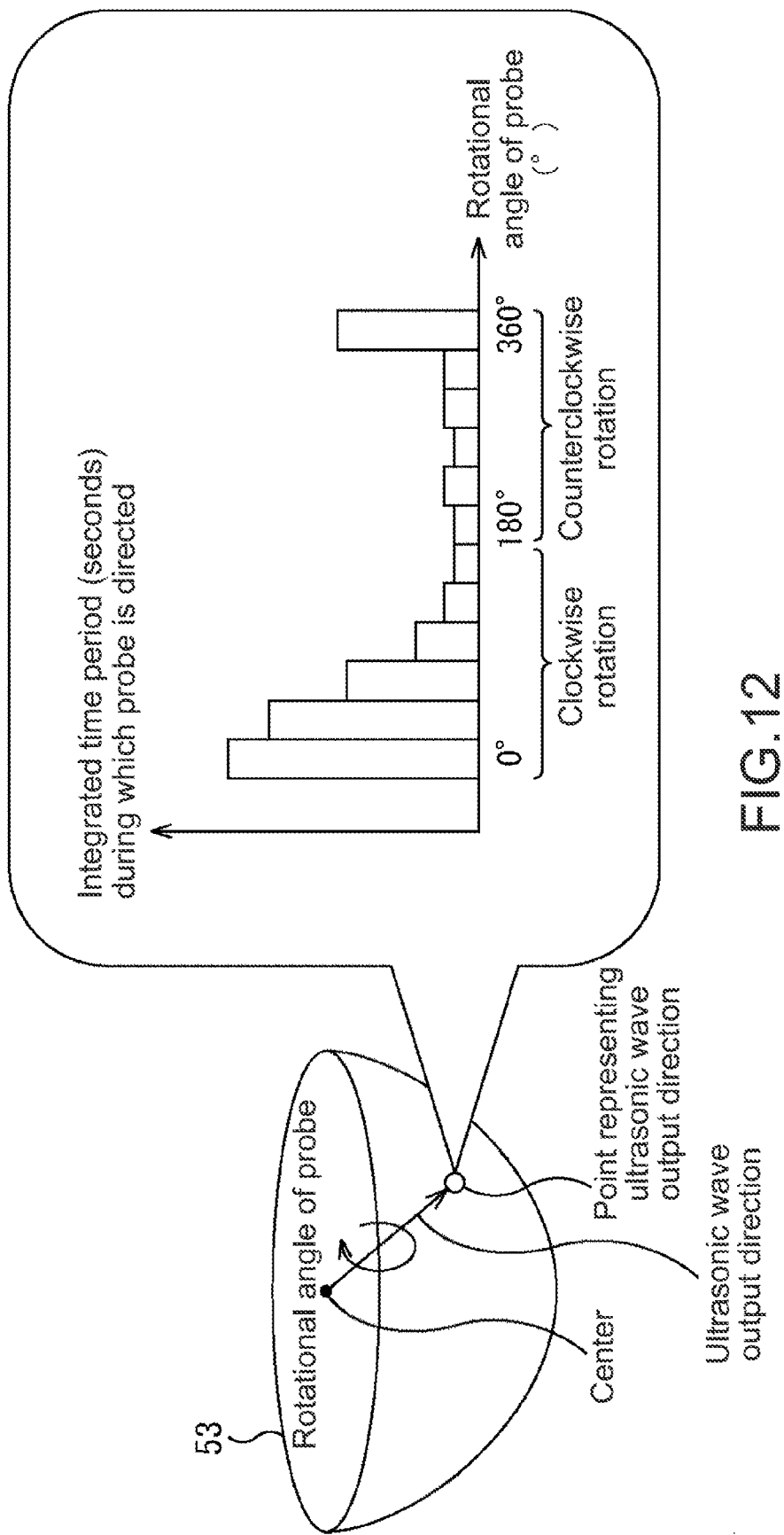
FIG. 12 is a diagram for describing rotation information.

FIG. 12 is a diagram for describing the rotation information.

As shown in FIG. 12, the ultrasonic wave output direction of the probe 10 in the state being directed from the center of the hemisphere as the spherical image 53 to a predetermined position on the surface of the hemisphere has a one-on-one correspondence with an intersection between the hemisphere as the spherical image 53 and a line extending from the center of the hemisphere in the ultrasonic wave output direction.

Therefore, each point on the hemisphere as the spherical image 53 represents the ultrasonic wave output direction that has a one-on-one correspondence with the point.

As the rotation information, as shown in FIG. 12, for example, an integrated time period (hereinafter, also referred to as integrated inspection time period) during which the probe 10 is put at each rotational angle can be adopted. The rotational angle is obtained when the probe 10 is rotated about an ultrasonic wave output direction represented by each point on the hemisphere as the spherical image 53.

The integrated inspection time period during which the probe 10 is put at each rotational angle about the ultrasonic wave output direction represented by each point on the hemisphere as the spherical image 53 (hereinafter, also referred to as a point on the spherical image 53) can be obtained using the total time period (T) during which the probe 10 at each posture is put on the inspection subject. The total time period (T) is stored as the status history of the probe 10 in the history storage unit 26.

As the rotational angle of the probe 10 about the ultrasonic wave output direction represented by each point on the spherical image 53, for example, values in the range of 0 to 360 degrees can be adopted. In the range, a rotational angle when the probe 10 is directed in the ultrasonic wave output direction is set to 0 degrees, and angles in clockwise rotation are set to be positive angles.

In this case, for example, it is assumed that the probe 10 is directed in an ultrasonic wave output direction represented by a certain point on the spherical image 53 and may be rotated clockwise and counterclockwise up to 180 degrees at the maximum about the ultrasonic wave output direction. In this case, a rotational angle when the probe 10 is rotated clockwise is in the range of 0 to 180 degrees, and a rotational angle when the probe 10 is rotated counterclockwise is in the range of 360 to 180 degrees.

In the case where an integrated inspection time period at each rotational angle is adopted as the rotation information, for example, the sum of all integrated inspection time periods in the range of 0 to 360 degrees, the sum of integrated inspection time periods in each predetermined range of rotational angles, e.g., 30 degrees each, can be adopted as an integrated inspection time period serving as the rotation information.

For example, in the case where the sum of all the integrated inspection time periods in the range of 0 to 360 degrees is adopted as the rotation information, the rotation information represents a time period (inspection time period) during which the probe 10 is being directed in the ultrasonic wave output direction represented by each point on the spherical image 53.

For example, in the case where the sum of all the integrated inspection time periods in the range of 180 degrees each is adopted as the rotation information, the rotation information represents a time period during which the probe 10 is rotated clockwise (rotated by a rotational angle in the range of 0 to 180 degrees) about the ultrasonic wave output direction represented by each point on the spherical image 53 and a time period during which the probe 10 is rotated counterclockwise (rotated by a rotational angle in the range of 360 to 180 degrees) about the ultrasonic wave output direction represented by each point on the spherical image 53.

As described above, each point on the hemisphere as the spherical image 53 represents an ultrasonic wave output direction that has a one-on-one correspondence with the point. Therefore, a rotation information image that represents rotation information on a rotation when the probe 10 is rotated about a certain ultrasonic wave output direction can be drawn at a point (hereinafter, referred to as corresponding point) on the hemisphere as the spherical image 53. The point represents the ultrasonic wave output direction.

Figure 13:
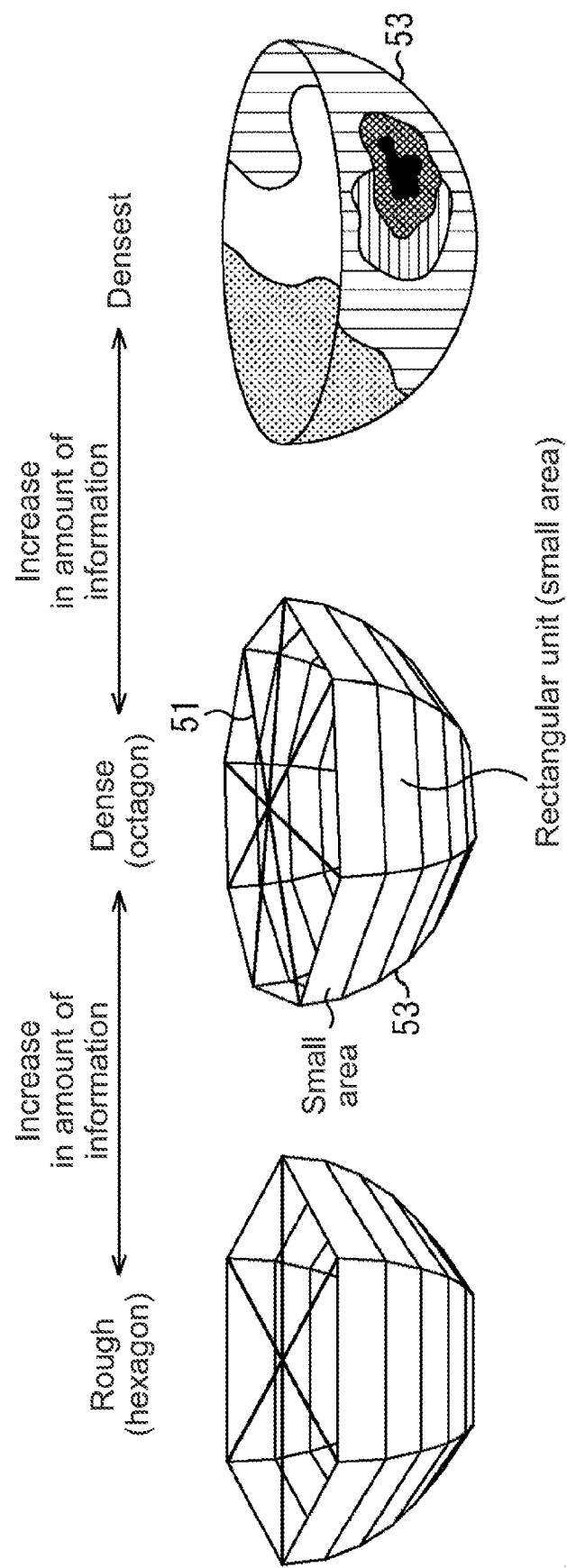
FIG. 13 is a diagram for describing the drawing of a rotation information image at a corresponding point.

FIG. 13 is a diagram for describing the drawing of a rotation information image at a corresponding point.

For example, in the case where the hemisphere as the spherical image 53 is sectioned into small areas each having a substantially rectangular shape as described with reference to FIG. 5, a rotation information image can be drawn in each of the small areas. The rotation information image represents rotation information on a rotation of the probe 10 about an ultrasonic wave output direction represented by a corresponding point included in the small area.

Here, as the rotation information on a rotation of the probe 10 about an ultrasonic wave output direction represented by a corresponding point included in a certain small area R (hereinafter, also referred to as rotation information of a small area R), for example, rotation information on a rotation of the probe 10 about an ultrasonic wave output direction represented by one corresponding point that is representative of corresponding points included in that small area R is adopted.

Further, as the rotation information of the small area R, for example, the sum of integrated inspection time periods for all corresponding points included in that small area R, the integrated inspection time periods each serving as the rotation information on the rotation of the probe 10 about an ultrasonic wave output direction represented by a corresponding point included in that small area R, can be adopted.

It is assumed that for example, as described with reference to FIG. 12, the sum of all the integrated inspection time periods in the range of 0 to 360 degrees, that is, a time period (inspection time period) during which the probe 10 is put in an ultrasonic wave output direction represented by a certain corresponding point, is adopted as rotation information on the rotation of the probe 10 about the ultrasonic wave output direction represented by the certain corresponding point. In this case, as the rotation information image, a rectangular unit that is an image having the same shape (rectangular shape) as the small area and is arranged to overlap each small area is adopted, and the brightness or color of the rectangular unit can be changed in accordance with the integrated inspection time period as the rotation information of the small area in which the rectangular unit is arranged.

It should be noted that as shown in FIG. 13, the size of the small area is adjustable in accordance with the capability (resource) of the ultrasonic inspection apparatus or an operation of a user. For example, the size of the small area can be reduced more as the capability of the ultrasonic inspection apparatus is higher.

In FIG. 13, the spherical image 53 on the left side has a larger size of the small area, that is, the small area becomes rougher, and the spherical image 53 on the right side has a smaller size of the small area, that is, the small area becomes finer.

As the size of the small area becomes smaller, the granularity of the rotation information image and of the rotation information becomes finer.

When the size of the small area becomes smaller and the small area is constituted of one pixel for example, each pixel of the spherical image 53 is drawn in brightness or color corresponding to the rotation information on the rotation of the probe 10 about an ultrasonic wave output direction. In the ultrasonic wave output direction, the position of the pixel is set as a corresponding point.

Figure 14:
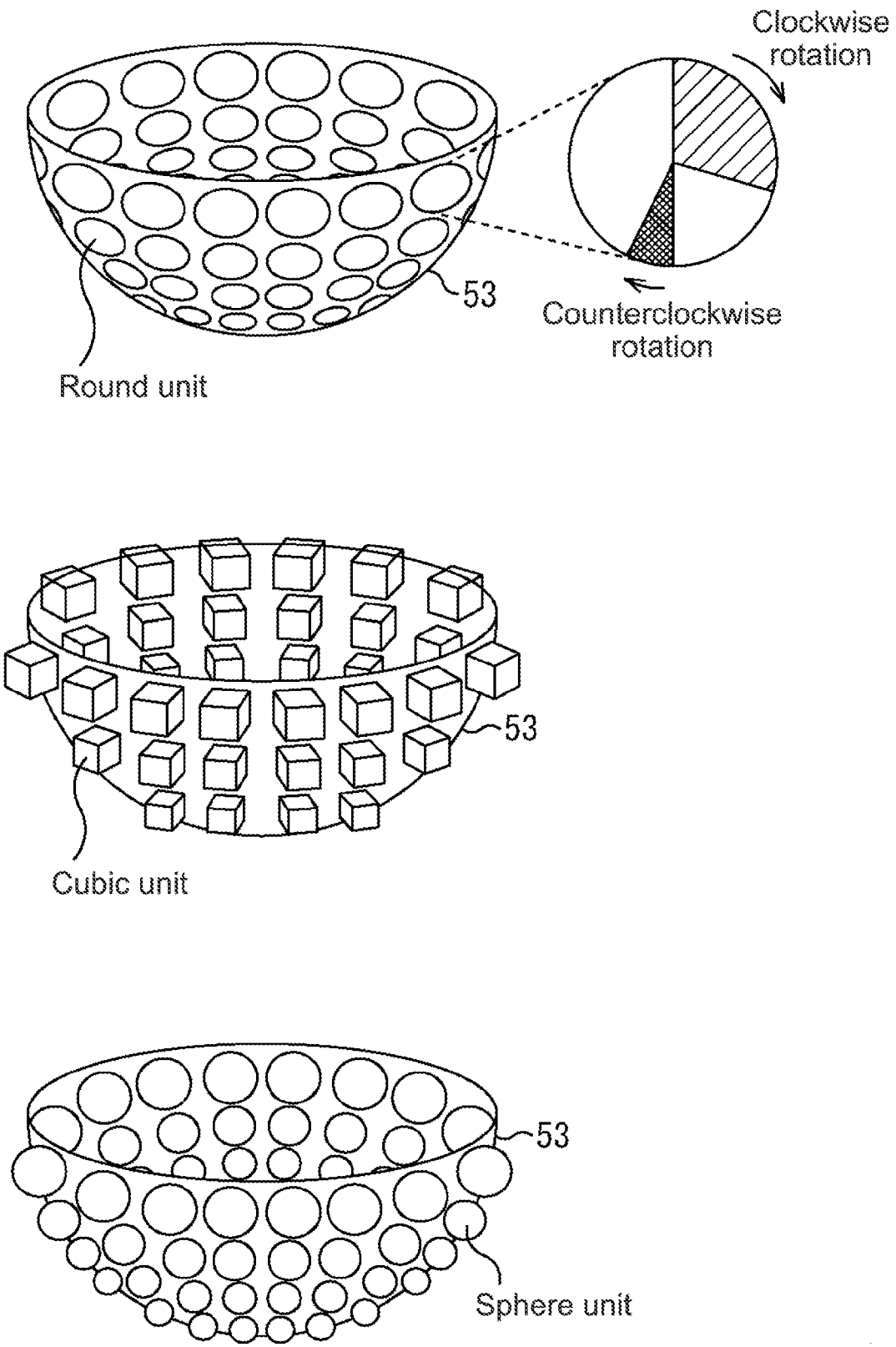
FIG. 14 is a diagram showing a display example of the spherical image in which an image other than a rectangular unit is adopted as the rotation information image.

FIG. 14 is a diagram showing a display example of the spherical image 53 in which an image other than the rectangular unit is adopted as the rotation information image.

As the rotation information image, for example, a round unit, a cubic unit, and a sphere unit can be adopted in addition to the rectangular unit.

Here, the round unit is a round image that is arranged in each small area of the spherical image 53 and has the size that fits within the small area. The cubic unit is a cubic image that is arranged in each small area of the spherical image 53 and has the size that fits within the small area. The sphere unit is a spherical image that is arranged in each small area of the spherical image 53 and has the size that fits within the small area.

It is assumed that for example, the sum of all integrated inspection time periods in the range of 0 to 360 degrees, that is, a time period (inspection time period) during which the probe 10 is put in an ultrasonic wave output direction represented by a certain corresponding point, is adopted as rotation information on a rotation of the probe 10 about the ultrasonic wave output direction represented by the certain corresponding point. In this case, for example, the round unit as the rotation information image changes in accordance with the inspection time period as rotation information of a small area in which the round unit is arranged.

Specifically, for example, as the integrated inspection time period as rotation information of a small area is longer, the inspection status image generation unit 32 draws a larger-size round unit as a round unit to be arranged in the small area.

The same holds true for the cubic unit and the sphere unit.

In the case where the round unit is adopted as the rotation information image, and for example, a time period during which the probe 10 is rotated clockwise and a time period during which the probe 10 is rotated counterclockwise, which are described with reference to FIG. 12, are adopted as rotation information on a rotation of the probe 10 about an ultrasonic wave output direction represented by a certain corresponding point, the inspection status image generation unit 32 can draw a round unit as seen in FIG. 14 in an enlarged manner.

Specifically, the inspection status image generation unit 32 can draw a round unit having a right-side semicircle and a left-side semicircle. In the right-side semicircle of a circle as the round unit, a sector portion with a central angle corresponding to the time period during which the probe 10 is rotated clockwise is painted. In the left-side semicircle of the circle as the round unit, a sector portion with a central angle corresponding to the time period during which the probe 10 is rotated counterclockwise is painted.

Figure 15:
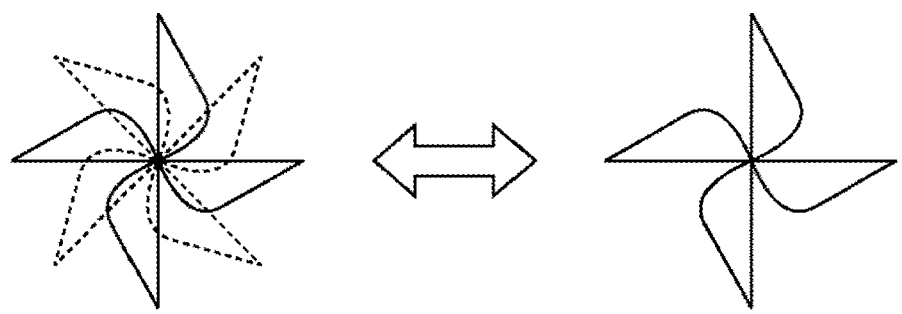
FIG. 15 is a diagram showing a display example of a pinwheel unit as another rotation information image.

FIG. 15 is a diagram showing a display example of a pinwheel unit as another rotation information image.

As the rotation information image, a pinwheel unit can be adopted in addition to the rectangular unit, the round unit, the cubic unit, and the sphere unit described above.

The pinwheel unit is an image in the shape of a pinwheel. The pinwheel unit is an image that has the size fitting within a small area of the spherical image 53 and is arranged in each small area of the spherical image 53, as in the case of the round unit and the like.

In the case where for example, a time period during which the probe 10 is rotated clockwise and a time period during which the probe 10 is rotated counterclockwise, which are described with reference to FIG. 12, are adopted as rotation information on a rotation of the probe 10 about an ultrasonic wave output direction represented by a certain corresponding point, and when the pinwheel unit is adopted as the rotation information image, the inspection status image generation unit 32 changes a rotating speed of the pinwheel as the pinwheel unit in accordance with the time period during which the probe 10 is rotated clockwise and the time period during which the probe 10 is rotated counterclockwise, for example. Additionally, the inspection status image generation unit 32 changes a rotation direction of the pinwheel as the pinwheel unit in accordance with the time period during which the probe 10 is rotated clockwise, the time period during which the probe 10 is rotated counterclockwise, and a magnitude relation.

It should be noted that a triangular pyramid unit having a triangular pyramid shape can be adopted as the rotation information image other than the above-mentioned units, for example. In the case where a triangular pyramid unit is adopted as the rotation information image, the inspection status image generation unit 32 changes the size of the triangular pyramid unit in accordance with the time period during which the probe 10 is rotated clockwise and the time period during which the probe 10 is rotated counterclockwise. Additionally, the inspection status image generation unit 32 changes a direction of a vertex of the triangular pyramid unit in accordance with the time period during which the probe 10 is rotated clockwise, the time period during which the probe 10 is rotated counterclockwise, and a magnitude relation.

Figure 16:
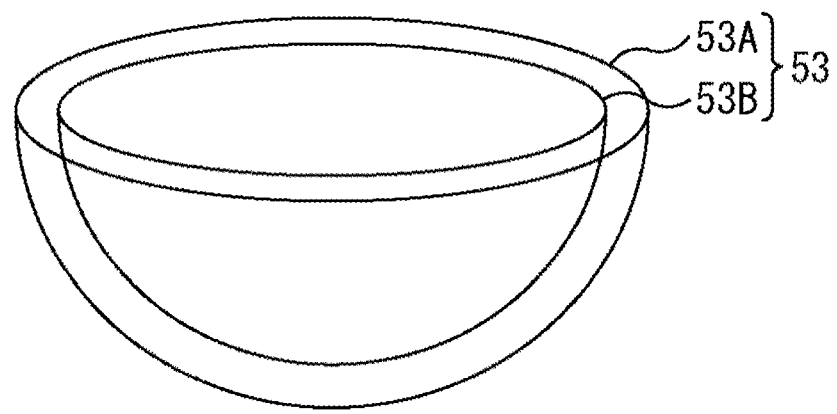
FIG. 16 is a diagram showing another example of the spherical image.

FIG. 16 is a diagram showing another example of the spherical image 53.

In FIG. 16, the spherical image 53 is formed of two layers, an outer hemisphere image 53A and an inner hemisphere image 53B.

In the spherical image 53 formed of the two layers as described above, a rotation information image of one of the clockwise rotation and the counterclockwise rotation can be arranged on one of the outer hemisphere image 53A and the inner hemisphere image 53B, and a rotation information image of the other rotation can be arranged on the other hemisphere image.

Specifically, for example, a spherical unit or the like whose size is changed in accordance with the time period of the clockwise rotation can be arranged on the outer hemisphere image 53A to serve as an rotation information image of the clockwise rotation, and a spherical unit or the like whose size is changed in accordance with the time period of the counterclockwise rotation can be arranged on the inner hemisphere image 53B to serve as an rotation information image of the counterclockwise rotation.

In the case where the spherical image 53 is formed of two layers, it is desirable to properly adjust the degree of transparency on the front side in order to ensure the visibility on the deep side.

As described above, in the ultrasonic inspection apparatus shown in FIG. 1, the foreground image including the linear image 51, the probe image 52, and the spherical image 53 is arranged within the three-dimensional space to be displayed as an inspection status image. Then, for example, the linear image 51 is changed in accordance with the status of the probe 10 as shown in FIGS. 6, 8, and the like. Thus, the operator can easily grasp an inspection status of the ultrasonic inspection.

Further, in the ultrasonic inspection apparatus shown in FIG. 1, for example, the texture of the spherical image 53 is changed in accordance with the inspection time period of the ultrasonic inspection as described with reference to FIG. 10. Thus, any inspection can be prevented from being omitted.

Further, in the ultrasonic inspection apparatus shown in FIG. 1, for example, the message for advice on the inspection method is displayed as described with reference to FIG. 7. Thus, the operator can understand a more appropriate operation for the probe 10.

It should be noted that in the ultrasonic inspection apparatus shown in FIG. 1, the status of the probe 10 and the status history of the probe 10 (hereinafter, also referred to as probe status information) that are used to generate the inspection status image in the inspection status image generation unit 32 can be stored in the storage 30.

In this case, using probe status information obtained when an ultrasonic inspection has been performed previously on an inspection subject, an inspection status image is generated and displayed. Thus, the operator can perform an ultrasonic inspection in the same quality as in the previous ultrasonic inspection.

Further, using probe status information obtained when a skilled operator has performed an ultrasonic inspection, an inspection status image is generated and displayed. Thus, the technique of an unskilled operator in the ultrasonic inspection can be improved.

In addition thereto, for example, inspection status images generated using probe status information obtained when different operators perform ultrasonic inspections are compared to each other. Thus, the technique of each operator in the ultrasonic inspection can be evaluated to be good or poor.

It should be noted that in the ultrasonic inspection apparatus shown in FIG. 1, an image showing parameters such as the depth of a vertex and a focus position of the probe 10 can be included in the inspection status image and displayed.

(Description on Computer to which Embodiment of Present Disclosure is Applied)

The series of processing described above can be performed by hardware or software. In the case where the series of processing is performed by software, a program constituting the software is installed in a general-purpose computer and the like.

Figure 17:
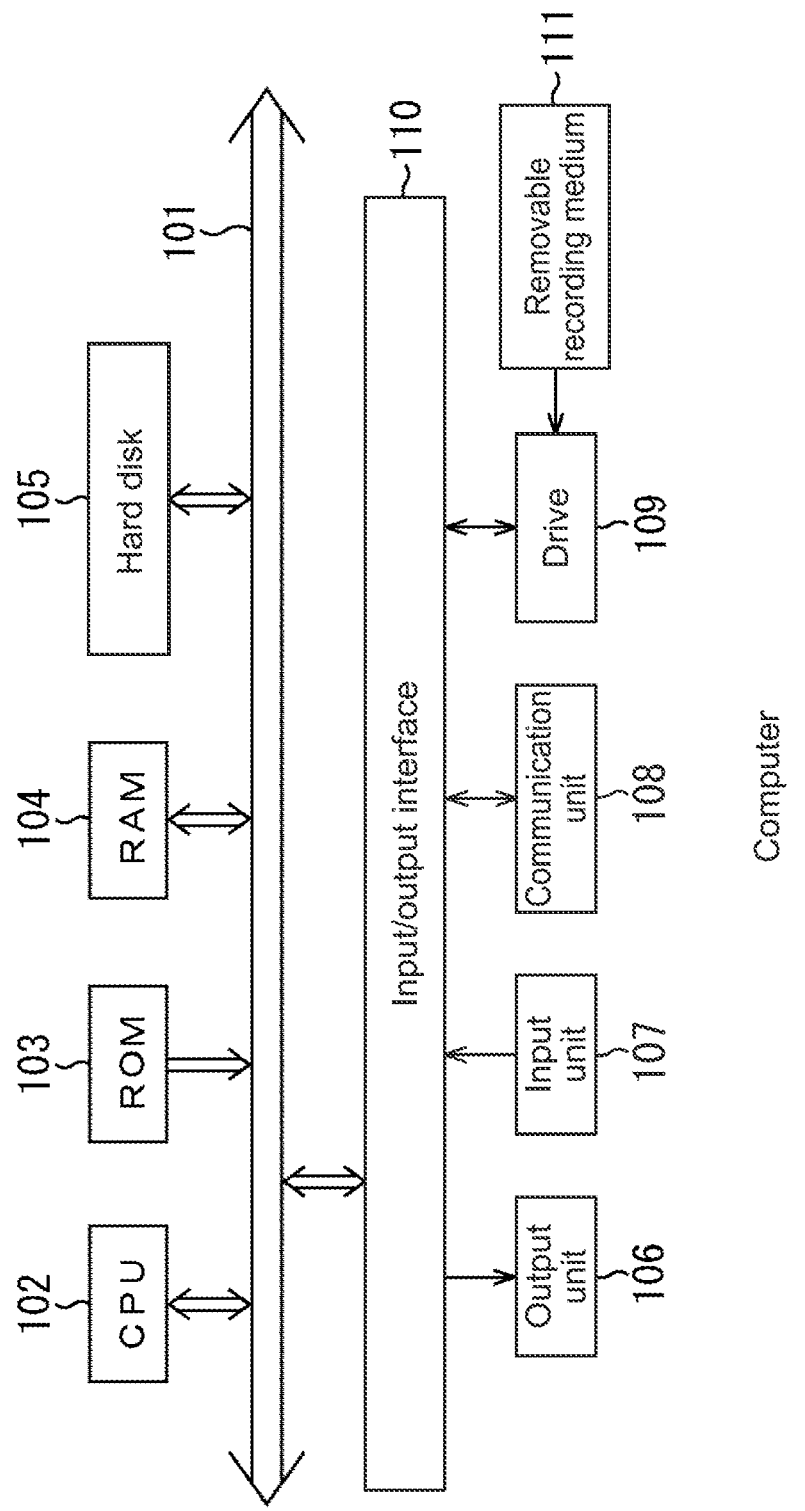
FIG. 17 is a block diagram showing a configuration example of an embodiment of a computer to which an embodiment of the present disclosure is applied.

In this regard, FIG. 17 shows a configuration example of an embodiment of a computer in which a program for executing the series of processing described above is installed.

The program can be stored in advance in a hard disk 105 or a ROM (Read Only Memory) 103 as a built-in recording medium of the computer.

Alternatively, the program can be stored (recorded) in (on) a removable recording medium 111. Such a removable recording medium 111 can be provided as so-called package software. Here, examples of the removable recording medium 111 include a flexible disc, a CD-ROM (Compact Disc Read Only Memory), an MO (Magneto Optical) disc, a DVD (Digital Versatile Disc), a magnetic disc, and a semiconductor memory.

It should be noted that the program can be installed from the removable recording medium 111 as described above in the computer, or can be downloaded in the computer via a communication network or a broadcast network and then installed in the built-in hard disk 105. In other words, for example, the program can be transferred wirelessly to the computer from a download site via a satellite for digital satellite broadcasting or can be transferred to the computer by cable via a network such as a LAN (Local Area Network) and the Internet.

The computer incorporates a CPU (Central Processing Unit) 102. The CPU 102 is connected with an input/output interface 110 via a bus 101.

When receiving, via the input/output interface 110, a command input by a user operating an input unit 107, for example, the CPU 102 executes the program stored in the ROM 103 according to the command. Alternatively, the CPU 102 loads the program stored in the hard disk 105 to a RAM (Random Access Memory) 104 and then executes the program.

Accordingly, the CPU 102 performs the processing according to the flowchart described above or the processing performed by the configuration of the block diagram described above. Then, as appropriate, the CPU 102 causes an output unit 106 to output a processing result or causes a communication unit 108 to transmit the processing result via the input/output interface 110, or causes the hard disk 105 to record the processing result thereon, for example.

It should be noted that the input unit 107 is constituted of a keyboard, a mouse, a microphone, and the like. Further, the output unit 106 is constituted of an LCD (Liquid Crystal Display), a speaker, and the like.

Here, in this specification, the processing performed by the computer according to the program is not necessarily performed in chronological order along the order described as the flowchart. Specifically, the processing performed by the computer according to the program includes processing executed in parallel or individually (for example, parallel processing or processing by object).

Further, the program may be processed by one computer (processor) or distributed and processed by a plurality of computers. Further, the program may be transferred to a distant computer and then executed thereby.

It should be noted that the embodiment of the present disclosure is not limited to the embodiment described above and can be variously modified without departing from the gist of the present disclosure.

For example, the present disclosure can have a configuration of cloud computing in which a plurality of apparatuses share one function and cooperate to perform processing via a network.

Further, the steps described in the flowchart described above can be executed by one apparatus or shared and executed by a plurality of apparatuses.

In addition, in the case where one step includes a plurality of processing steps, the plurality of processing steps in one step can be executed by one apparatus or shared and executed by a plurality of apparatuses.

It should be noted that the present disclosure can take the following configurations.

(1) An image processing apparatus, including
a display controller configured to arrange a foreground image in a three-dimensional space and display, on a display device, the foreground image as an inspection status image representing an inspection status by an ultrasonic wave, the foreground image including
    a linear image being as an image including a plurality of linear images that change in accordance with a status of a probe and connect the center of a circle and a circumference of the circle with each other,
    a probe image that is located at the center of the circle and has a shape of the probe, and
    a spherical image being as a spherical image that represents a range to which the ultrasonic wave output from the probe is applied and has a cross section as the circle.

(2) The image processing apparatus according to (1), in which
the display controller is configured to deflect a plurality of lines serving as the linear image in accordance with a pressure of the probe being put on an inspection subject of an ultrasonic inspection.

(3) The image processing apparatus according to (1) or (2), in which
the display controller is configured to twist a plurality of lines serving as the linear image in accordance with an amount of twist of the probe being put on an inspection subject of an ultrasonic inspection.

(4) The image processing apparatus according to any one of (1) to (3), in which
the spherical image includes wireframe.

(5) The image processing apparatus according to any one of (1) to (4), in which
the foreground image includes a direction image representing a direction of the ultrasonic wave output by the probe located at the center of the circle.

(6) The image processing apparatus according to any one of (1) to (5), in which
the display controller is configured to change a texture of a predetermined position in accordance with an inspection time period in a direction from the center of the circle to the predetermined position on a surface of a sphere as the spherical image.

(7) The image processing apparatus according to any one of (1) to (6), in which
the display controller is configured to move the foreground image within the three-dimensional space along with a movement of the probe.

(8) The image processing apparatus according to any one of (1) to (7), in which
the foreground image includes an rotation information image representing information of a rotation of the probe when the probe directed from the center of the circle to a predetermined position on a surface of a sphere as the spherical image is rotated about a direction in which the ultrasonic wave is output.

(9) The image processing apparatus according to any one of (1) to (8), in which
the display controller is configured to change the probe image in accordance with a change of the status of the probe.

(10) The image processing apparatus according to any one of (1) to (9), in which
the display controller is configured to display a message for advice on an inspection method, based on the status of the probe.

(11) The image processing apparatus according to (10), in which
the display controller is configured to display the message based on one of a pressure of the probe being put on an inspection subject of an ultrasonic inspection and an inspection time period in a direction from the center of the circle to a predetermined position on a surface of a sphere as the spherical image.

(12) An image processing method, including
arranging a foreground image in a three-dimensional space and displaying, on a display device, the foreground image as an inspection status image representing an inspection status by an ultrasonic wave, the foreground image including
    a linear image being as an image including a plurality of linear images that change in accordance with a status of a probe and connect the center of a circle and a circumference of the circle with each other,
    a probe image that is located at the center of the circle and has a shape of the probe, and
    a spherical image being as a spherical image that represents a range to which the ultrasonic wave output from the probe is applied and has a cross section as the circle.

The present disclosure contains subject matter related to that disclosed in Japanese Priority Patent Application JP 2012-114010 filed in the Japan Patent Office on May 18, 2012, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An image processing apparatus, comprising at least one processor configured to:
    arrange a foreground image in a three-dimensional space; and
    display, on a display device, the foreground image as an inspection status image representing an inspection status by an ultrasonic wave, the foreground image including
        a linear image being an image including a plurality of lines that connect the center of a circle and a circumference of the circle with each other, wherein the center of the circle corresponds to a position of a probe being put on a subject for an ultrasonic inspection, and wherein one or more lines of the linear image change in accordance with a status of the probe,
        a probe image that is located at the center of the circle and has a shape of the probe, and
        a spherical image being as a spherical image that represents a range to which the ultrasonic wave output from the probe is applied and has a cross section as the circle.

2. The image processing apparatus according to claim 1, wherein the at least one processor is configured to deflect the plurality of lines serving as the linear image in accordance with a pressure of the probe.

3. The image processing apparatus according to claim 1, wherein the at least one processor is configured to twist the plurality of lines serving as the linear image in accordance with an amount of twist of the probe.

4. The image processing apparatus according to claim 1, wherein the spherical image includes wireframe.

5. The image processing apparatus according to claim 1, wherein the foreground image includes a direction image representing a direction of the ultrasonic wave output by the probe located at the center of the circle.

6. The image processing apparatus according to claim 1, wherein the at least one processor is configured to change a texture of a predetermined position, on a surface of a sphere as the spherical image, in accordance with an inspection time period in a direction from the center of the circle to the predetermined position.

7. The image processing apparatus according to claim 1, wherein the at least one processor is configured to move the foreground image within the three-dimensional space along with a movement of the probe.

8. The image processing apparatus according to claim 1, wherein the foreground image includes an rotation information image representing information of a rotation of the probe when the probe directed from the center of the circle to a predetermined position on a surface of a sphere as the spherical image is rotated about a direction in which the ultrasonic wave is output.

9. The image processing apparatus according to claim 1, wherein the at least one processor is configured to change the probe image in accordance with a change of the status of the probe.

10. The image processing apparatus according to claim 1, wherein the at least one processor is configured to display a message for advice on an inspection method, based on the status of the probe.

11. The image processing apparatus according to claim 10, wherein the at least one processor is configured to display the message based on one of a pressure of the probe and an inspection time period in a direction from the center of the circle to a predetermined position on a surface of a sphere as the spherical image.

12. The image processing apparatus according to claim 1, wherein the status of the probe includes a pressure of the probe, a position of the probe, a direction of the probe, a movement speed in a translation direction of the probe.

13. The image processing apparatus according to claim 1, wherein the at least one processor is configured to detect the status of the probe at predetermined intervals using one or more sensors.

14. An image processing method, comprising
arranging a foreground image in a three-dimensional space and displaying, on a display device, the foreground image as an inspection status image representing an inspection status by an ultrasonic wave, the foreground image including
a linear image being an image including a plurality of lines that connect the center of a circle and a circumference of the circle with each other, wherein the center of the circle corresponds to a position of a probe being put on a subject for an ultrasonic inspection, and wherein one or more lines of the linear image change in accordance with a status of the probe,
a probe image that is located at the center of the circle and has a shape of the probe, and
a spherical image being as a spherical image that represents a range to which the ultrasonic wave output from the probe is applied and has a cross section as the circle.

* * * * *